(12) United States Patent
Bashkirov et al.

(10) Patent No.: US 10,329,598 B2
(45) Date of Patent: Jun. 25, 2019

(54) METHODS AND APPARATUSES FOR NUCLEIC ACID SHEARING BY SONICATION

(71) Applicant: LIFE TECHNOLOGIES CORPORATION, Carlsbad, CA (US)

(72) Inventors: Vladimir I. Bashkirov, Davis, CA (US); Umberto Ulmanella, Foster City, CA (US); Robert G. Eason, Los Gatos, CA (US); Bradford J. Taft, San Francisco, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 634 days.

(21) Appl. No.: 14/816,920

(22) Filed: Aug. 3, 2015

(65) Prior Publication Data

US 2015/0337300 A1    Nov. 26, 2015

Related U.S. Application Data

(62) Division of application No. 12/372,464, filed on Feb. 17, 2009, now Pat. No. 9,127,306.

(60) Provisional application No. 61/029,113, filed on Feb. 15, 2008.

(51) Int. Cl.
| | | |
|---|---|---|
| *C07H 21/02* | (2006.01) | |
| *C12Q 1/6806* | (2018.01) | |
| *C07H 1/06* | (2006.01) | |
| *C07H 21/00* | (2006.01) | |
| *C12N 15/10* | (2006.01) | |

(52) U.S. Cl.
CPC ............ *C12Q 1/6806* (2013.01); *C07H 1/06* (2013.01); *C07H 21/00* (2013.01); *C12N 15/1093* (2013.01)

(58) Field of Classification Search
USPC ......... 435/6.1, 6.11, 91.1, 183; 436/94, 501; 536/23.1, 24.3, 24.33
See application file for complete search history.

(56) References Cited

U.S. PATENT DOCUMENTS

| | | | |
|---|---|---|---|
| 5,689,052 A | 9/1997 | Brown et al. | |
| 5,766,608 A * | 6/1998 | Kolattukudy | C07K 14/285 424/242.1 |
| 6,117,846 A * | 9/2000 | Li | A61Q 17/04 424/59 |
| 6,235,501 B1 | 5/2001 | Gautsch et al. | |
| 6,333,406 B1 | 12/2001 | Inselburg et al. | |
| 6,440,725 B1 | 8/2002 | Pourahmadi et al. | |
| 6,578,659 B2 | 6/2003 | Manna et al. | |
| 6,719,449 B1 | 4/2004 | Laugharn, Jr. et al. | |
| 6,869,336 B1 * | 3/2005 | Hardikar | B24B 37/0056 252/79.1 |
| 6,948,843 B2 | 9/2005 | Laugharn, Jr. et al. | |
| 9,127,306 B2 | 9/2015 | Bashkirov et al. | |
| 2001/0039014 A1 | 11/2001 | Bass et al. | |
| 2002/0068872 A1 | 6/2002 | Manna et al. | |
| 2002/0113534 A1 * | 8/2002 | Hayashi | G02B 6/0036 313/113 |
| 2002/0127587 A1 | 9/2002 | Simms et al. | |
| 2002/0177137 A1 | 11/2002 | Hodge | |
| 2004/0236253 A1 * | 11/2004 | Vortman | A61N 7/02 601/2 |
| 2005/0048477 A1 * | 3/2005 | Peng | C12Q 1/6897 506/14 |
| 2006/0014192 A1 | 1/2006 | Hodge | |
| 2006/0035251 A1 | 2/2006 | Young et al. | |
| 2006/0147520 A1 * | 7/2006 | Ruegg | A61K 9/0073 424/464 |
| 2009/0208919 A1 * | 8/2009 | Utermohlen | B82Y 5/00 435/2 |
| 2009/0233814 A1 | 9/2009 | Bashkirov et al. | |

FOREIGN PATENT DOCUMENTS

| | | |
|---|---|---|
| WO | 2002065125 | 2/2002 |
| WO | 2006032952 | 3/2006 |
| WO | 2009/103068 A1 | 8/2009 |

OTHER PUBLICATIONS

"TE buffer" from Wikipedia, the free encyclopedia. Printed on Jul. 29, 2017.*
Stratagene Catalog (1988), p. 39. Published by Stratgene, 11011 North Torrey Pines Road, La Jolla, CA 92037, USA.*
Bankier, A, "Generation of Random Fragments by Sonication", *Methods Mol Bio*, vol. 23, DNA Sequencing Protocols, 1993, pp. 47-50.
Farnham, P. , "Chromatin Immunoprecipitation", *(ChIPs) Cloning Protocol (Farnham Lab) (ChIPs) Cloning Protocol (Farnham Lab)* (Feb. 19, 2007), UC Davis , XP002534474, Feb. 19, 2007.
Fuciarelli, A et al., "Induction of Base Damage in DNA Solutions by Ultrasonic Cavitation", *Free Radical Biology & Medicine*, vol. 18(2), 1995, pp. 231-238.
Golemis, E. A. et al., "Protein-Protein Interactions: A Molecular Cloning Manual", 2005 , *Cold Spring Harbor Laboratory*,XP009119069 ISBN: 978-0879697235 paragraph 2, p. 70.
Milowska, K et al., "Reactive oxygen species and DNA damage after ultrasound exposure", *Biomolecular Engineering*, 24, 2007, pp. 263-267.
Mitchell, C. M. et al., "Prostaglandin H synthase-2 gene regulation in the amnion at labour: histone acetylation and nuclear factor kappa B binding to the promoter inVivo", *Molecular Human Reproduction*, vol. 14, no., XP002534472 ISSN: 1360-9947 the whole document, Molecular Human Reproduction; ISSN: 1360-9947, Jan. 1, 2008, pp. 53-59.
Oefner, P et al., "Efficient random subcloning of DNA sheared in a recirculating point-sink flow system", *Nuc Acids Res*, vol. 24(20), 1996, pp. 3879-3886.
PCT/US2009/34301, "International Search Report and Written Opinion dated Jul. 20, 2009".

(Continued)

*Primary Examiner* — Frank W Lu

(57) ABSTRACT

Methods and kits for preparing nucleic acid fragments from a sample of purified nucleic acid are provided. Alternatively, chromatin or other long polymers can be sheared with similar methods and kits.

11 Claims, 27 Drawing Sheets

(56) References Cited

OTHER PUBLICATIONS

PCTUS200934301, "International preliminary report on Patentability and Written Opinion dated Aug. 26, 2010".
Rodriguez, L et al., "Hydrodynamic Shearing by VirTis Blending Conserves Nucleosome Structure of Rat Liver Chromatin", *Archives of Biochemistry and Biophysics*, vol. 200(1), 1980, 116-129.
Sambrook, J. et al., "Fragmentation of DNA by Sonication", *Cold Spring Harbor Laboratory*, XP009118981 Retrieved from the Internet: URL:http://cshprolocols.cshlp.org/cgi/cont entlfull/2006/23/pdb.prot4538> [retrieved on Jun. 26, 2009], 2006.

\* cited by examiner

METHODS AND APPARATUSES FOR NUCLEIC ACID SHEARING BY SONICATION

CROSS-REFERENCE TO RELATED APPLICATIONS

This application is a divisional of U.S. patent application Ser. No. 12/372,464 filed Feb. 17, 2009, now U.S. Pat. No. 9,127,306 B2, which claims a priority benefit under 35 U.S.C. § 119(e) from U.S. Patent Application No. 61/029,113, filed Feb. 15, 2008, which are incorporated herein by reference.

FIELD

Methods and apparatuses for nucleic acid fragmentation by sonication, more specifically mechanical DNA fragmentation by sonication with microparticles. The present teachings can be expanded to material for fragmentation that includes any substance including nucleic acid, for example chromatin that includes a nucleic acid and protein, and any long polymer, other than nucleic acid.

BACKGROUND

Nucleic acid shearing or fragmentation provides the a first step in several embodiments for constructing nucleic acid libraries, as well as, embodiments for hybridization of target nucleic acids on solid supports, for example microarrays. These embodiments benefit from controlled shearing forces to provide increased efficiency in fragmentation and subsequent analysis. Nucleic acid, for example DNA or RNA, fragmentation are the focus of next-generation sequencing platforms such as those by 454 (Roche Molecular, Inc.), SOLiD (Applied Biosystems), and Solexa (Illumina, Inc.). These platforms each have different embodiments for nucleic acid fragmentation that determine different parameters such as efficiency of fragmentation, fragmentation time, fragment length distribution range, and quality of fragments generated. For example, double-stranded DNA may be accompanied by single-stranded (denatured) DNA, or damaged (depurinated) DNA. Furthermore, there are several applications of next-generation sequencing that would benefit from higher throughput that could be achieved by reducing the time needed to process each sample.

There are different methods for nucleic acid fragmentation. Nucleic acids can be fragmented chemically by enzymatic digestion, for example, by DNaseI. Nucleic acids can be fragmented mechanically, such as by hydrodynamic shearing or sonication. Mechanical fragmentation can occur by several methods known in the art, including shearing of DNA by passing it through the narrow capillary or orifice (Oefner et al., Nucleic Acids Res. 1996; Thorstenson et al., Genome Res. 1995), for example a hypodermic needle, sonicating the DNA, such as by ultrasound (Bankier, Methods Mol. Biol. 1993), grinding in cell homogenizers (Rodriguez L V. Arch Biochem Biophys. 1980), for example stirring in a blender, or nebulization. Mechanical fragmentation results, in some methods, in double strand breaks within a DNA molecule. Sonication is used widely for random fragmentation of nucleic acids for sequencing library or microarray probe preparations. A variety of instruments available on the market can provide sonication for nucleic acid preparation. Sonication may also be performed using any convenient approach, e.g., with a multi-tip sonicator or using acoustic sound waves. A Microplate Sonicator® (Misonix Inc.) may be used to partially fragment the DNA. Such a device is described in U.S. Patent Publication No. 2002/0068872. Other examples of sonicators for nucleic acid fragmentation are Vialtweeter or Sonotrode. Another acoustic-based system that may be used to fragment DNA is described in U.S. Pat. Nos. 6,719,449, and 6,948,843 manufactured by Covaris Inc. U.S. Pat. No. 6,235,501 describes a mechanical focusing acoustic sonication method of producing high molecular weight DNA fragments by application of rapidly oscillating reciprocal mechanical energy in the presence of a liquid medium in a closed container, which may be used to mechanically fragment the DNA. An exemplary configuration of such an instrument is shown at FIG. 4 illustrating a concave transducer focusing the acoustic energy through a water bath to a focal zone in the sample liquid contained in the sample vessel. In various embodiments, the focused acoustic energy can have a frequency of 1.1 MHz with 400 Watts of power applied (100 Watt maximum at 20% duty cycle), on a volume of approximately 2 millimeters in diameter by 6 millimeters in height (depth by length). Sonication parameters (such as power, duty cycle, and cycles per burst can be adjusted in the process recipe through software settings. The sonication region shape and volume is hardware dependent and can be modified with hardware changes. Purified nucleic acids can be amplified prior to or after a fragmentation step.

The shearing of a nucleic acid molecule in a liquid medium is achieved through the hydrodynamic action of the liquid on the molecule itself. When a velocity gradient exists within the liquid medium, the shear stresses produced by the elongational components of the flow result into an aligning and extensional action on the nucleic acid molecules along the direction of the shear stresses.

When the applied hydrodynamic action (tensile forces, bending moments, etc) builds up to exceed the intrinsic strength of the polymeric chain, a breakage in the chain will result, giving rise to two fragments, each shorter than the original. In general, since the hydrodynamic action applied to the nucleic acid molecule is proportional to its length, it is increasingly difficult to shear a fragment of a nucleics acid as it becomes shorter and shorter. The shear stress "tau" τ in the fluid giving rise to the hydrodynamic action on the polymeric chain can be expressed according to the following formula:

$$\tau_{xy} = \mu \cdot \left( \frac{\partial u}{\partial y} + \frac{\partial v}{\partial x} \right)$$

where μ "mu" is the viscosity of the liquid medium and du/dy, and dv/dx, the velocity gradients within the flow field. In order to enhance the shearing action and thus decrease size fragment and increase shearing throughput, the shear stress can be increased by increasing the viscosity of the liquid medium or by increasing the velocity gradients within the flow field. High concentration glycerol solutions are normally used to increase the viscosity of the liquid medium by several orders of magnitude compared to pure water. In addition, mechanisms such as sonication, can be used to produce stronger flow fields than otherwise achievable through more basic mechanical devices. For example, the minimum fragment size obtained in a Hydroshear instrument, where the liquid is force through a small orifice, is of the order of hundreds of base pair. On the other hand, fragments as short as tens of base pairs can be easily obtained with a sonicator thanks to the violence of the flow generated by ultrasonic cavitation. Taking into account the shear being the sum of elongation and rotation to cause stretching and tumbling to produce scission. This results in 5'-CpG-3' preferential cleavage on double-stranded DNA (Grokhovsky, Mol. Bio., 2006). Typical parameters for optimizing nucleic acid fragmentation are sonication parameters (bursts per cycle, intensity, and duty cycle), process temperature, buffer viscosity, sample volume, nucleic acid amount, sample vessel size and material, buffer ionic strength, and nucleic acid purification method.

Varying lengths of fragments can be provided depending on the sequencing platform. For example, the Illumine 1G sequencing platform requires the sonication of pure DNA to generate 100-300 bp pieces for fragment libraries, and of chromatin to get fragments in 200-700 bp range for ChIP-sequencing, using i.e. 250 Sonifier (Branson) or Bioruptor (Diagenode AS). Another example, SOLiD used sonication for fragment library preparation to generate size ranges of 60 to 90 base pair fragments from purified nucleic acids. This can be achieved with a Covaris, Inc. S2 sonicator fragmenting the nucleic acid for 40 minutes at maximum setting for power and frequency. Exploiting such instruments at maximum capacity for long periods of time, such as those needed to process each nucleic acid sample, can accelerate instrument aging visible as decline in instrument performance. Further, 40 minute fragmentation cycles (like in the SOLiD protocol) limit the throughput for sequencing instruments by extending the time necessary for gene library generation. In addition, sonication of purified nucleic acids is carried out in glycerol or other viscous liquids to increase the friction on the nucleic acids. However, the glycerol is then separated from the nucleic acid fragments. This process requires chemical extraction and can reduce the recovery of the nucleic acid fragments. Furthermore, long fragmentation cycles under high power settings increases the probability and extent of damage and denaturation of the purified nucleic acids (Milowska et al., Biomolecular Engineering 2007). This can be attributed to cavitation induced by sonication. Cavitation can collapse microbubbles, produce microjets, or produce shock waves in the sample liquid, as well as, generating strong flow, localized temperature rise, production of free radicals, for example H and OH (Fuciarelli et al, Free Radical Biology & Medicine, 1995).

It is desirable to provide a method for preparing nucleic acid fragments from a sample of purified nucleic acid that reduces the length of fragmentation time. It is desirable to provide a method for preparing nucleic acid fragments from a sample of purified nucleic acid that avoids glycerol or other viscous liquids and fragments the nucleic acid in an aqueous solution. It is desirable to increase the recovery of fragmented nucleic acids by reducing the power settings of sonicators or reducing the loss of nucleic acid fragments to post-fragmentation separation. It is also desirable to improve sequencing results by reducing the bias of sonication toward certain fragment sizes or fragment types (as opposed to the randomness of nebulization or hydroshearing). The present invention provides these desired results with a method for preparing nucleic acid fragments from a sample of purified nucleic acid by adding particles to the sample and sonicating the suspension. It is counterintuitive that adding particles to the sample would provide the desired fragmentation because the increase in viscosity tends to stop the mechanism for fragmentation at certain point by greatly reducing the molecules spatial turnover in the focal point of sonication. Therefore, the desirable results of the present invention are not predictable based on current understanding of nucleic acid fragmentation.

Particles have been used with sonication to lyse cells, see for example U.S. Pat. No. 6,440,725 describing a cartridge for cell lysis using beads and an ultrasonic transducer. However, the application of particles in cell lysis via sonication cannot achieve nucleic acid fragmentation because of the cell lysate present. Furthermore, nucleic acid fragmentation is contrary to the goal of cell lysis for detecting low copy of DNA targets in large volume sample, i.e. for diagnostics. To detect low-copy nucleic acids targets after cell lysis it is desirable to have the extracted DNA in high molecular weight form, as excessive degradation by i.e. oversonication can dramatically reduce the average DNA fragment length below the length of amplicon, thus greatly reducing the sensitivity of such PCR-based diagnostic methods.

It is also desirable to provide shearing of material that contains some nucleic acid, for example chromatic with DNA and proteins. It is also desirable to provide shearing of other long polymers that are not organic in nature. The present teachings can be expanded to material for fragmentation that includes any substance including nucleic acid, for example chromatin that includes a nucleic acid and protein, and any long polymer, other than nucleic acid where applications require shearing of the polymer for further processing.

SUMMARY

In certain embodiments, a method for preparing nucleic acid fragments from a sample of purified nucleic acid is provided. In certain embodiments, a sample of purified nucleic acid is provided, particles are added to the sample, a suspension of the sample and the particles is sonicated, and the nucleic acid fragments are collected.

In certain embodiments, a method for preparing a gene library from nucleic acid extraction is provided. In certain embodiments, a sample of purified nucleic acid is provided, particles are added to the sample, no nonaqueous solvents are added to the sample, a suspension of the sample and the particles is sonicated, and the nucleic acid fragments are collected.

In certain embodiments, a method for preparing nucleic acid fragments from a sample of purified nucleic acid is provided. In certain embodiments, a sample of purified nucleic acid is provided which does not include cell lysates, particles are added to the sample, a suspension of the sample and the particles is sonicated, and the nucleic acid fragments are collected.

In certain embodiments, a kit for preparing nucleic acid fragments from a sample of purified nucleic acid is provided. In certain embodiments, an aqueous buffer solution is included, wherein the solution is substantially free of nonaqueous solvents, and monodisperse particles are included for addition to the buffer solution and the sample of purified nucleic acid.

The present teachings can be expanded to material for fragmentation that includes any substance including nucleic acid, for example chromatin that includes a nucleic acid and protein, and any long polymer, other than nucleic acid where applications require shearing of the polymer for further processing. These and other features of the present teachings are set forth herein.

DETAILED DESCRIPTION OF CERTAIN EMBODIMENTS

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents defines a term that contradicts that term's definition in this application, this application controls.

The use of the singular includes the plural unless specifically stated otherwise. The word "a" or "an" means "at least one" unless specifically stated otherwise. The use of "or" means "and/or" unless stated otherwise. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

Figure 3:
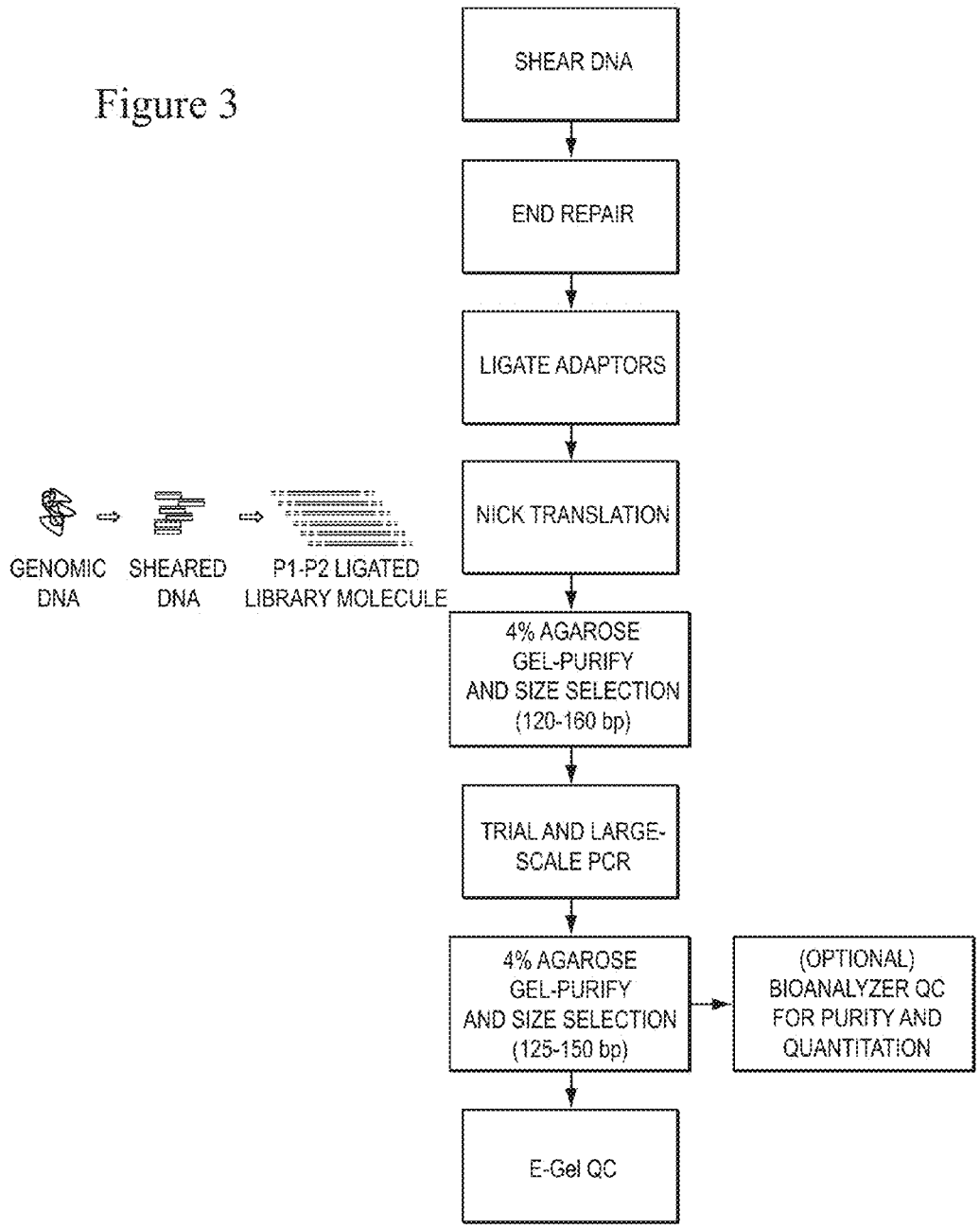
FIG. 3 shows a non-limiting exemplary protocol for short fragment library preparation.
Figure 4:
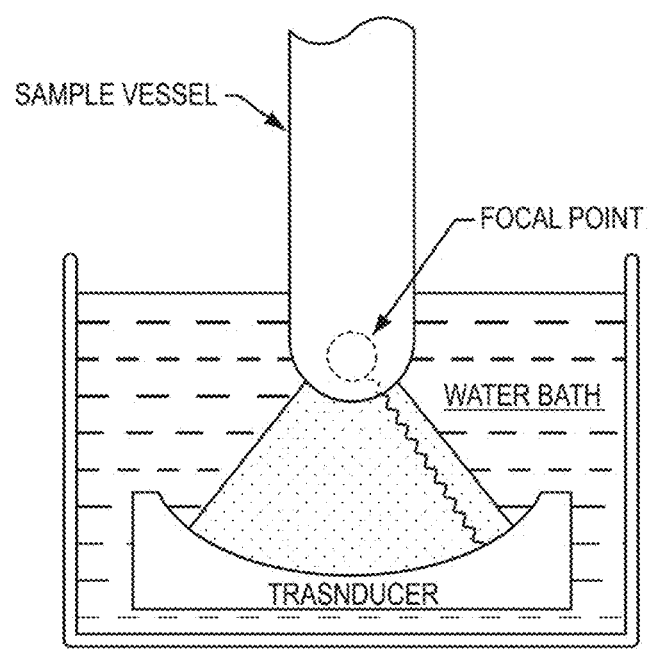
FIG. 4 shows a non-limiting exemplary apparatus for focusing acoustic sonication.

According to various embodiments, FIG. 3 illustrates an exemplary protocol for DNA fragment library preparation, for example SOLiD sequencing platform. The process shown takes genomic DNA that has been purified to remove any cellular material that resulted from lysis to extract the genomic DNA. The DNA is then sheared to provide fragments. The typical shearing protocol includes taking a 500 microliter sample that contains 10 micrograms of DNA in an 85% glycerol solution, and using a Covaris sonicator to generate roughly 100 watts of energy for a 40 minutes cycle. The DNA is sheared and then the ends are repaired and ligated with adaptors and undergo nick translation to create P1-P2 ligated library molecules. Nick translation removes any nicks left in the dsDNA molecules during upstream steps of library construction in order to allow for efficient final PCR amplification of the library (see Large scale PCR step in FIG. 3). The library containing a mixture Case No. 7001 9 of molecules of various sizes is then resolved upon 4% agarose gel electrophoresis and molecules in 120-160 base pair range are size selected and extracted from agarose. The library can be subjected to trial and large-scale PCR and then further purification. The library is then taken to quality control by for example electrophoretic gel or a Bioanalyzer (Agilent Technologies). According to various embodiments, a method of forming a released paired tag from a DNA fragment of interest is provided. The method comprises ligating a first adaptor to a first end of a DNA fragment of interest and ligating a second adaptor to a second end of the DNA fragment of interest, thereby producing an adaptor modified fragment, circularizing the adaptor modified fragment by attaching a third adaptor to the adaptor modified fragment, thereby forming a circular nucleic acid molecule wherein a first nick is present between the third adaptor and the first adaptor and a second nick is present between the second adaptor and the third adaptor, wherein the circular nucleic acid molecule comprises a first strand and a second strand of DNA, and wherein the first nick and the second nick are not present on the same strand of the circular nucleic acid molecule; performing a nick translation reaction wherein a nick on each strand of the circular nucleic acid molecule is translated into the DNA fragment of interest, and cleaving the circular nucleic acid molecule at a position at a translated nick, thereby forming a released paired tag. Additional examples are contained in copending application titled, "METHOD OF MAKING A PAIRED TAG LIBRARY FOR NUCLEIC ACID SEQUENCING" with Ser. No. 12/350,837, filed Jan. 8, 2009, now, U.S. Pat. No. 8,530,197 B2.

TE buffer is a commonly used buffer solution in molecular biology, especially in procedures involving DNA or RNA. It is called "TE" buffer because it contains Tris, a common pH buffer, and EDTA, a molecule chelating cations like Mg2+. The purpose of TE buffer is to protect DNA or RNA from degradation. A typical recipe for making TE buffer is: 10 mM Tris, bring to pH 7.5 with HCl, 1 mM EDTA. Based on nuclease studies from the 80's, the pH is usually adjusted to 7.5 for RNA and 8.0 for DNA. The respective DNA and RNA nucleases are supposed to be less active at these pH values. But pH 8.0 can safely be used for storage of both DNA and RNA. EDTA further inactivates nucleases, by binding to metal ions required by these enzymes.

Definitions

As used herein, the terms "nucleic acid" means single-stranded and double-stranded polymers of nucleotide monomers, including, but not limited to, 2'-deoxyribonucleotides and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Nucleic acids can be natural nucleic acids, artificial nucleic acids, analogs thereof, or combinations thereof. Nucleic acids have associated counter ions, such as H+, NH4+, trialkylammonium, Mg2+, Na+ and the like. A nucleic acid can be composed entirely of deoxyribonucleotides, entirely of ribonucleotides, or chimeric mixtures thereof. Nucleic acid can be comprised of nucleobase and sugar analogs. Nucleic acid typically range in size from a few monomeric units, e.g. 5-40 when they are more commonly frequently referred to in the art as oligonucleotides, to several thousands of monomeric nucleotide units. Unless denoted otherwise, whenever a nucleic acid sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine.

Nucleic acids are said to have "5' ends" and "3' ends" because mononucleotides are reacted to make nucleic acids in a manner such that the 5' phosphate of one mononucleotide pentose ring is attached to the 3' oxygen of its neighbor in one direction via a phosphodiester linkage. Therefore, an end of a nucleic acid is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger nucleic acid, also can be said to have 5' and 3' ends.

As used herein, "purified nucleic acid" denotes a genomic polynucleotide without cellular material. For example, a sample from a cell, where the polynucleotide is fragmented into acceptable sizes to serve as nucleic acid fragments. The options and variations of purification of the genomic polynucleotide are broadly known to one skilled in the art of cellular lysis and vary on the cellular material and inhibitors that can be contained in that material.

As used herein, the term "chromatin" encompasses complex of DNA and protein that makes up chromosomes. It is found inside the nuclei of eukaryotic cells, and within the nucleoid in prokaryotes. The major proteins involved in chromatin are histone proteins, although many other chromosomal proteins have prominent roles too. The term also encompasses DNA/protein/RNA complex extracted from eukaryotic lysed interphase nuclei. Just which of the multitudinous substances present in a nucleus will constitute a part of the extracted material will depend in part on the technique each researcher uses. Furthermore, the composition and properties of chromatin vary from one cell type to the another, during development of a specific cell type, and at different stages in the cell cycle. The term also encompasses DNA double helix in the cell nucleus is packaged by special proteins termed histones. The formed protein/DNA complex is called chromatin. The structural entity of chromatin is the nucleosome.

Chromatin is DNA plus the proteins (and RNA) that package DNA within the cell nucleus.

As used herein, the term "microarray" encompasses an arrangement of polynucleotides present on a solid support or in an arrangement of vessels. Certain array formats are referred to as a "chip" or "biochip" (M. Schena, Ed. Microarray Biochip Technology, BioTechnique Books, Eaton Publishing, Natick, Mass. (2000)). An array can comprise a low-density number of addressable locations, e.g. 1 to about 12, medium-density, e.g. about a hundred or more locations, or a high-density number, e.g. a thousand or more. Typically, the array format is a geometrically-regular shape that allows for fabrication, handling, placement, stacking, reagent introduction, detection, and storage. The array can be configured in a row and column format, with regular spacing between each location. Alternatively, the locations can be bundled, mixed, or homogeneously blended for equalized treatment and/or sampling. An array can comprise a plurality of addressable locations configured so that each location is spatially addressable for high-throughput handling, robotic delivery, masking, and/or sampling of reagents and/or by detection means including scanning by laser illumination and confocal and/or deflective light gathering. The array can comprise one or more "addressable locations," e.g., "addressable positions," that is, physical locations that comprise a known type of molecule.

Certain Exemplary Embodiments

In each of the following embodiments, markers were used for 15 base pairs and 1500 base pairs to demonstrate the relationship between time in seconds on the x-axis and the length of nucleic acid fragments in base pairs. These will be reflected as sharp spikes at the ends of each graph.

Certain Exemplary Embodiments of Sonication

Figure 1:
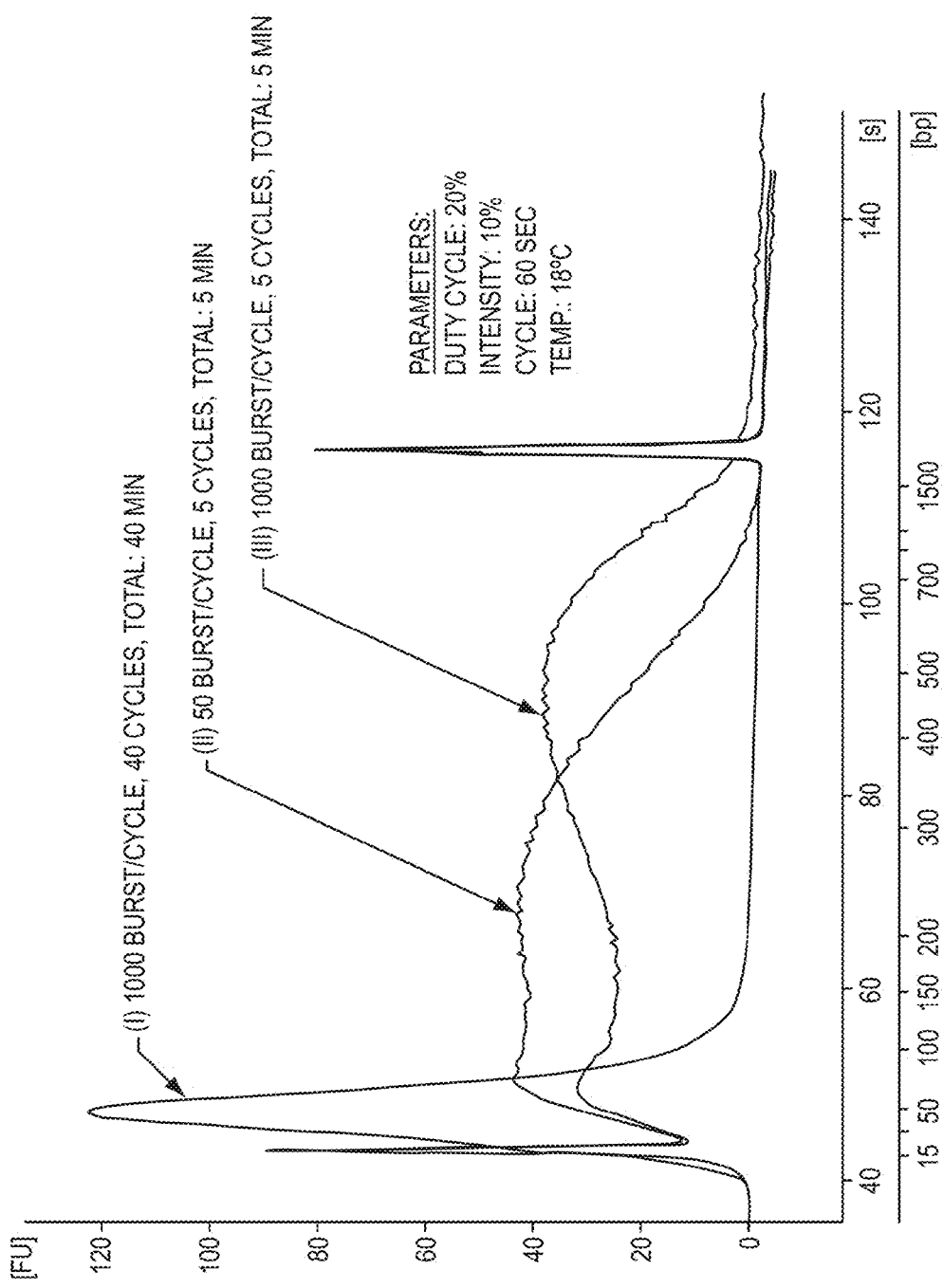
FIG. 1 shows a graph of DNA fragmentation using existing methods of sonication.
Figure 2:
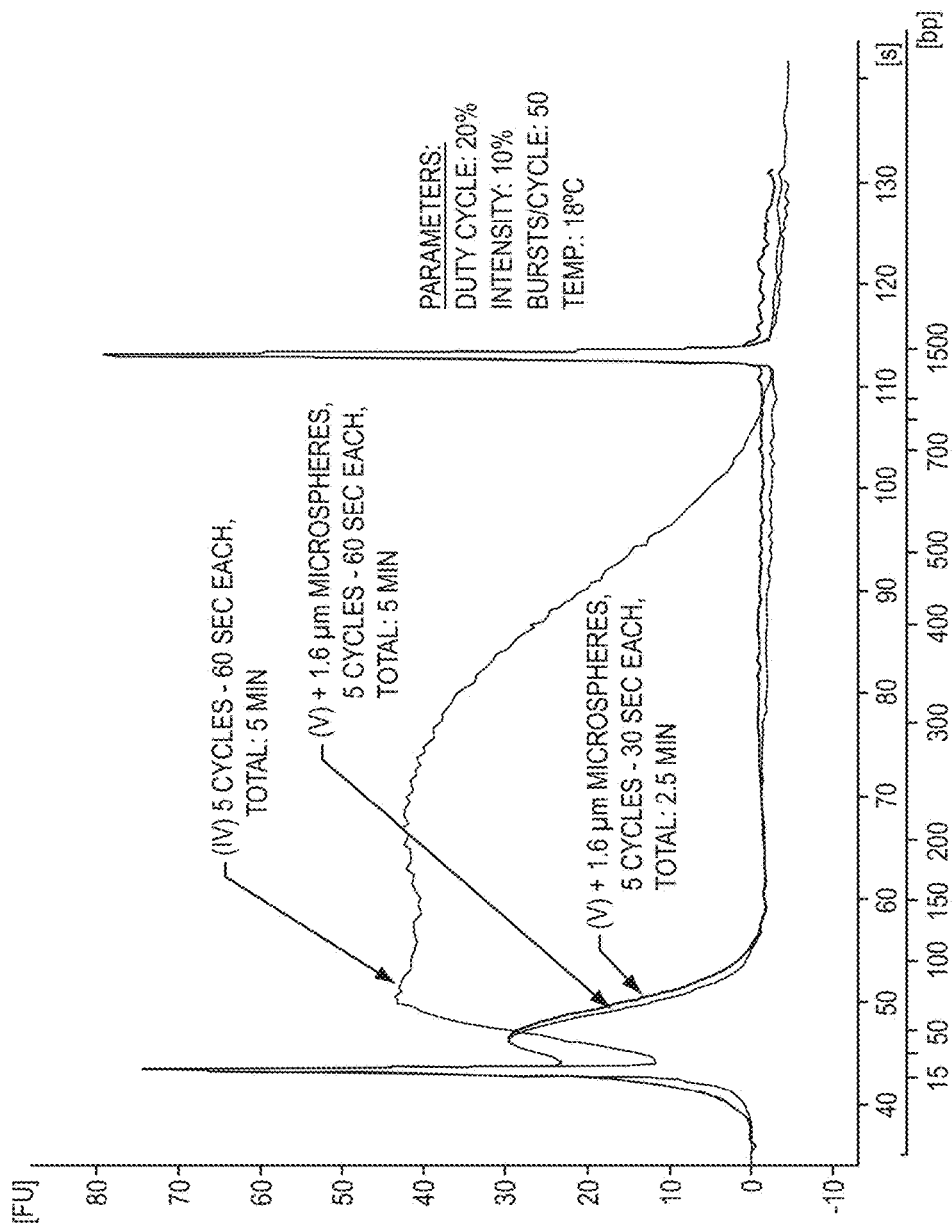
FIG. 2 shows a graph of DNA fragmentation comparing existing methods and non-limiting exemplary methods of the present invention.

In various embodiments according to the present invention, a method for nucleic acid fragmentation is provided which includes adding particles to the sample of purified nucleic acid. The present invention has demonstrated accelerated fragmentation times of at least 8 fold to at least 16 fold. For example, the standard 40 minutes sonication was significantly shortened. The analysis for fragmentation, according to various embodiments, was measured using DNA 100 Assay chips and reagents (Agilent) on a Bioanalyzer (Agilent). FIG. 1 illustrates nucleic acid fragmentation in 85% glycerol with parameters of 20% duty cycle, intensity of 10%, cycle of 60 seconds, and temperature of 18 degrees Celcius. The curve (I) shows the size distribution of fragments generated after a standard 40 minute procedure used in SOLiD at the highest acoustic frequency of 1000 bursts per cycle. The high molecular weight (for example greater than 15,000 bases) genomic DNA was converted to short fragments (peak at 48 base pairs). The curve (III) shows the same conditions except for reducing the time to 5 minutes. The fragmented nucleic acid is spread between the 15 base pair and 1500 based pair markers with a majority remaining in the high size range (peak at approximately 500 base pairs). The curve (II) shows an embodiment decreasing the frequency to 50 bursts per cycle that shifted the fragment distribution towards the low range compared to curve (III) but still not providing a majority of DNA fragments in the desired range of 60 base pairs to 90 base pairs, for example in preparing a fragment library for SOLiD. Curve (II) is also shown on FIG. 2 as curve (IV).

Figure 5:
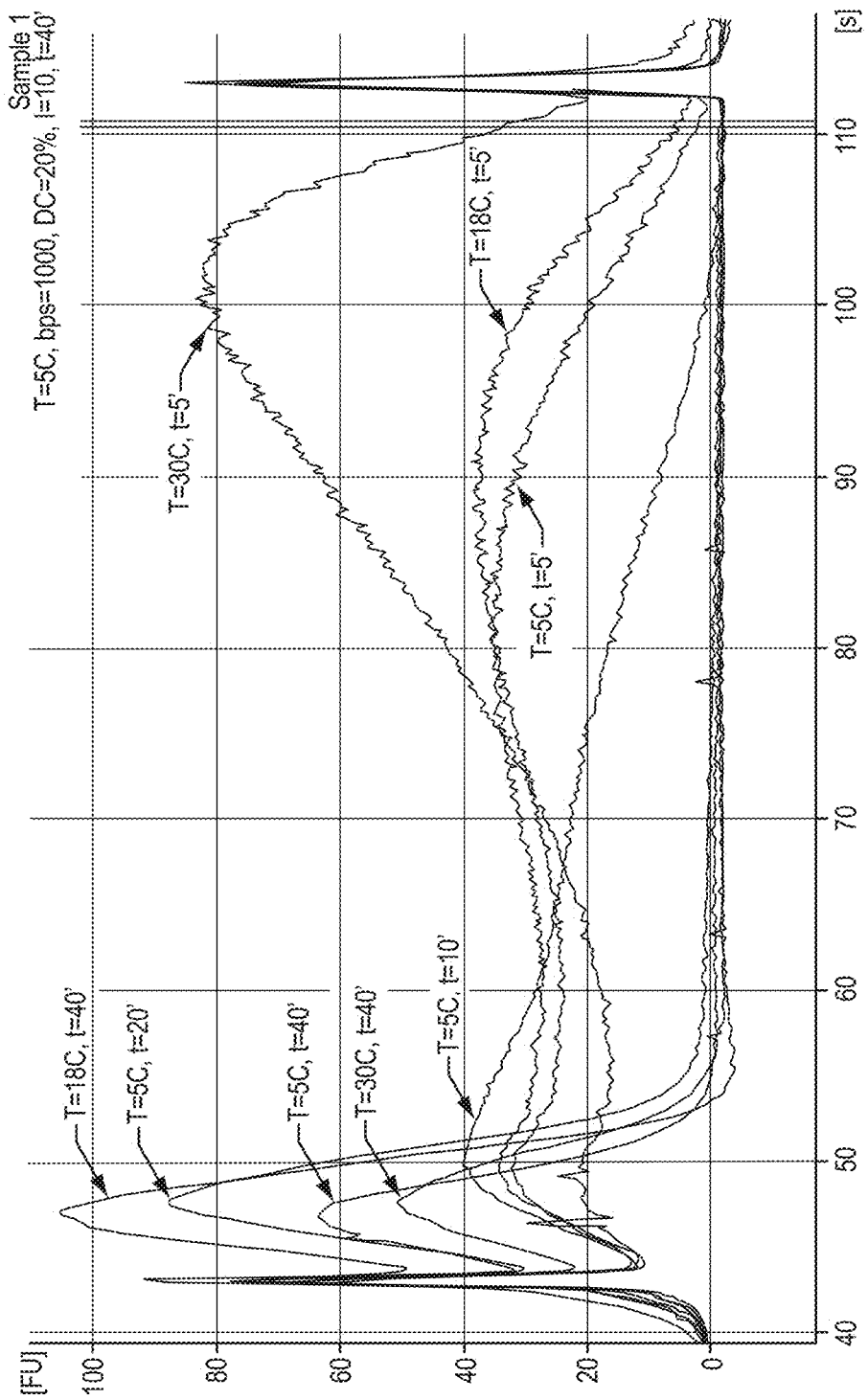
FIG. 5 shows a graph demonstrating the effects of temperature on fragmentation.
Figure 6:
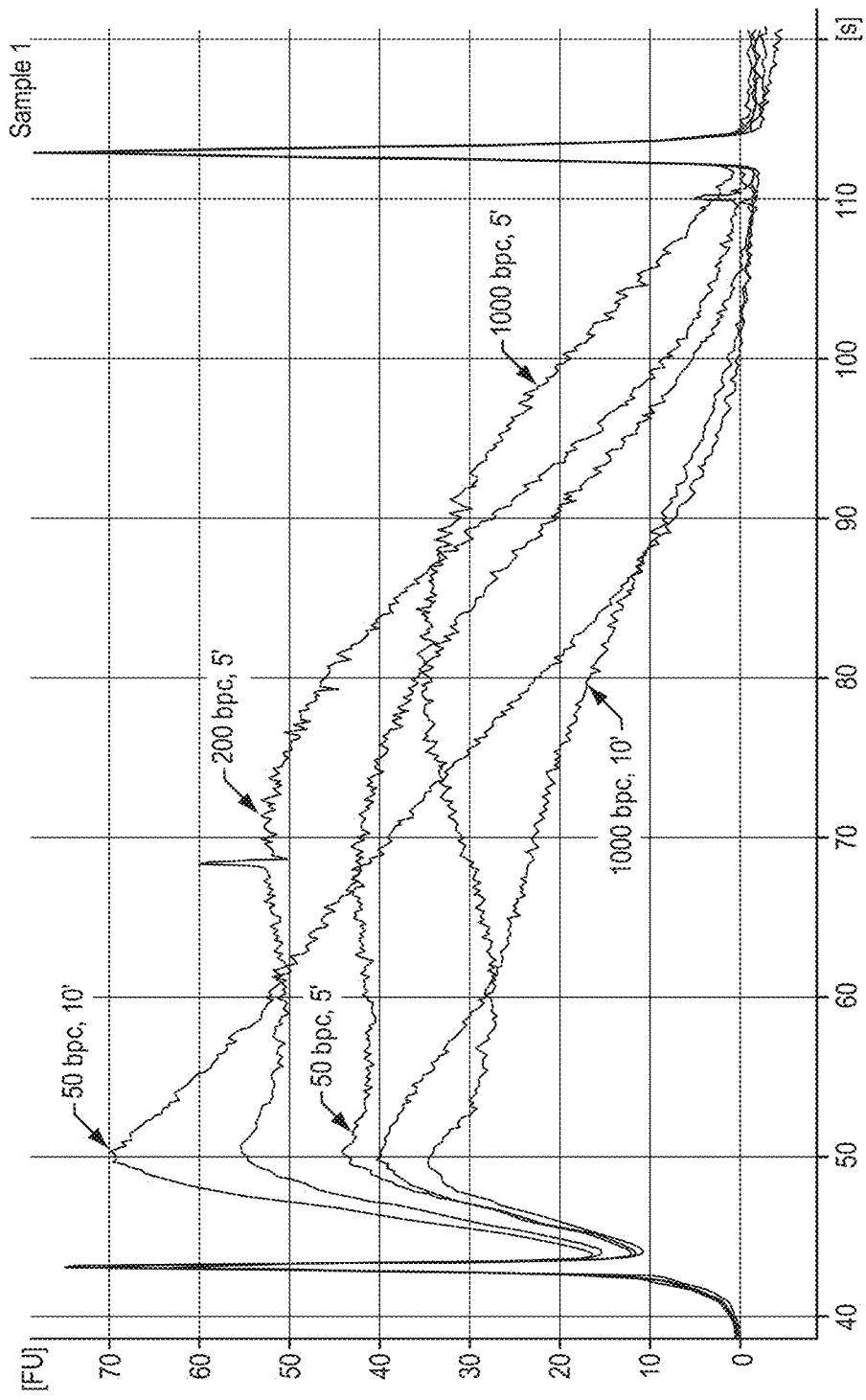
FIG. 6 shows a graph demonstrating the effects of bursts per cycle on fragmentation.
Figure 7:
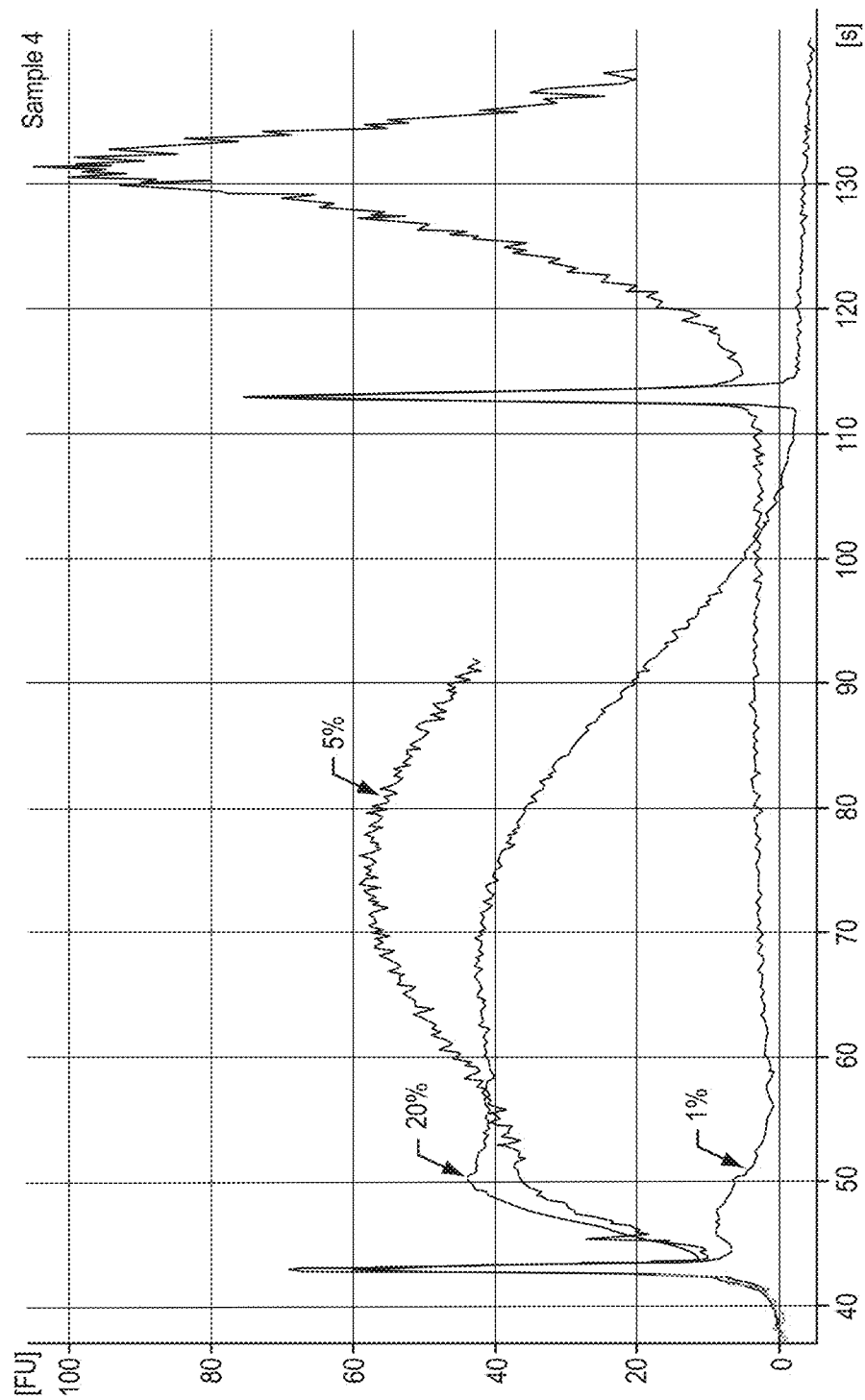
FIG. 7 shows a graph demonstrating the effects of duty cycle on fragmentation.

In various embodiments, the following standard SOLiD protocol test conditions were followed: DNA amount of 10 micrograms, *E. coli* strain Novablue (Novagen) DNA as sample nucleic acid, phenol-chloroform DNA purification method, 500 microliter sample volume, 85% glycerol, 1.6 micrometer monodispersed glass particles (Duke Scientific) vial sample vessel with dimensions of 65 millimeters by 13 millimeters. The sonication parameters were 40 minutes, at 20% duty cycle with intensity of 10, and 1000 bursts per cycle. FIG. 5 illustrates a graph showing temperature in degrees Celsius and time in minutes. This embodiment demonstrates that even if sample temperature were to vary, time is the dominant parameter. The parameter of 18 degrees Celsius was selected for other exemplary embodiments. FIG. 6 illustrates a graph showing the effect of frequency (bursts per cycle) and time in minutes on shearing of DNA. This embodiment demonstrates that lower bursts per cycle provide the highest yield for the desired fragmentation at 60 base pairs to 90 base pairs. The parameter of 50 bursts per cycle was selected for other exemplary embodiments. FIG. 7 illustrates a graph showing the effect of duty cycle on fragmentation of nucleic acids. This embodiment demonstrates that duty cycle affects fragmentation. The parameter of 20% was selected for other exemplary embodiments.

Figure 12:
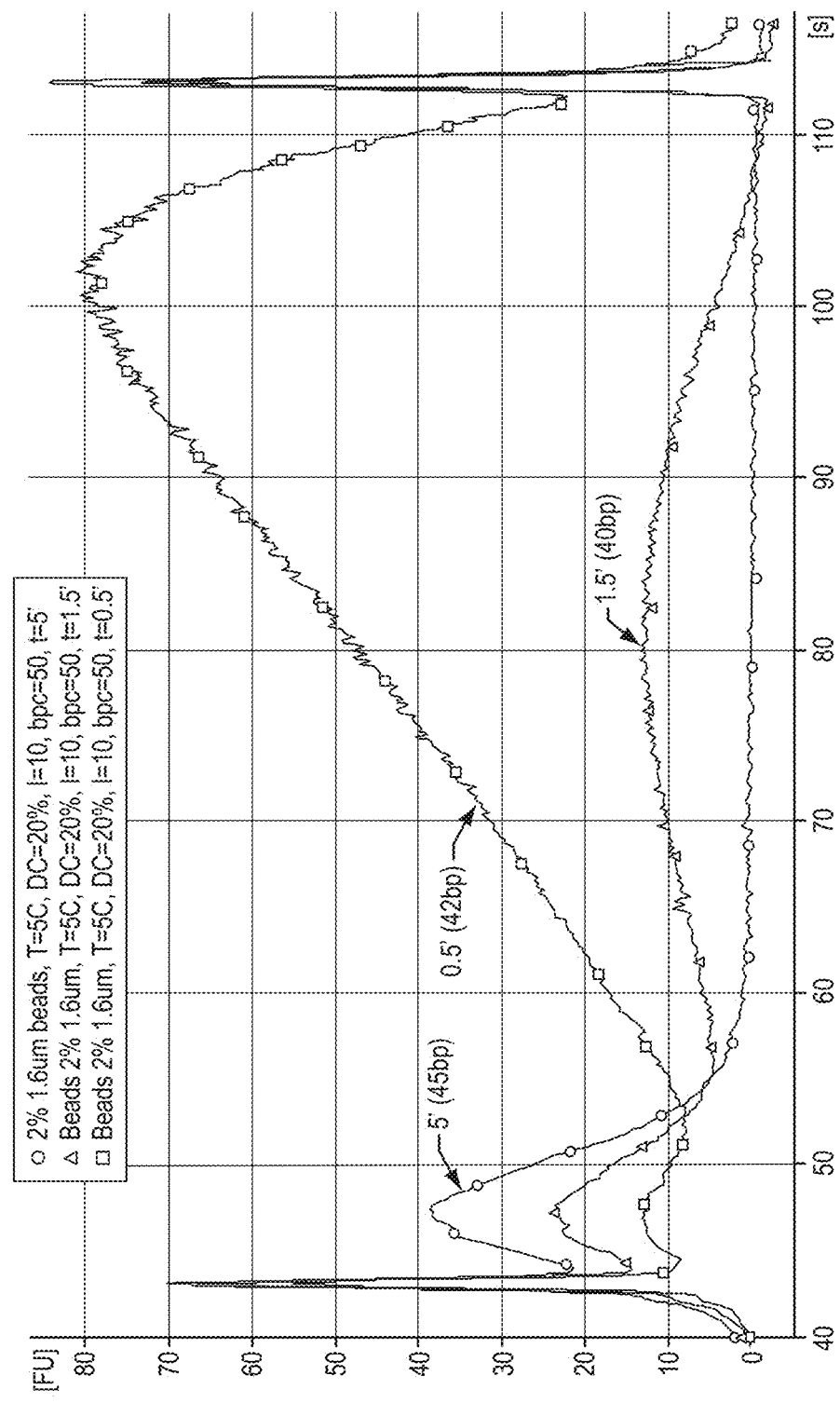
FIGS. 12, 14, and 19 show graphs demonstrating the effects of time on fragmentation.

In various embodiments, a Covaris S2 sonicator was used with glass tubes immersed in a water bath at 18 degrees Celcius. The sample included 500 microliters of 1×TE buffer pH 8.0, 10 micrograms of genomic DNA isolated from *E. coli* strain NovaBlue (Novagen), 85% glycerol, 1.6 micrometer monodispersed glass particles (Duke Scientific) were added to the sample (as dry powder) to provide a 5% (weight/volume) suspension to the embodiment of curve (IV) (same as curve (II) in FIG. 1) and fragmented the nucleic acid as shown in curve (V) of FIG. 2. Further time reduction to 2.5 minutes, as shown by curve (VI) was achieved without substantially changing the fragment size distribution shown in curve (V). In various embodiments, FIG. 12 illustrates a graph showing the minimization of time had on fragmentation. This embodiment demonstrated that duration for fragmentation shorter than 2 minutes decreased the fragmentation at the desired fragment sizes of 60 base pairs to 90 base pairs.

Figure 8:
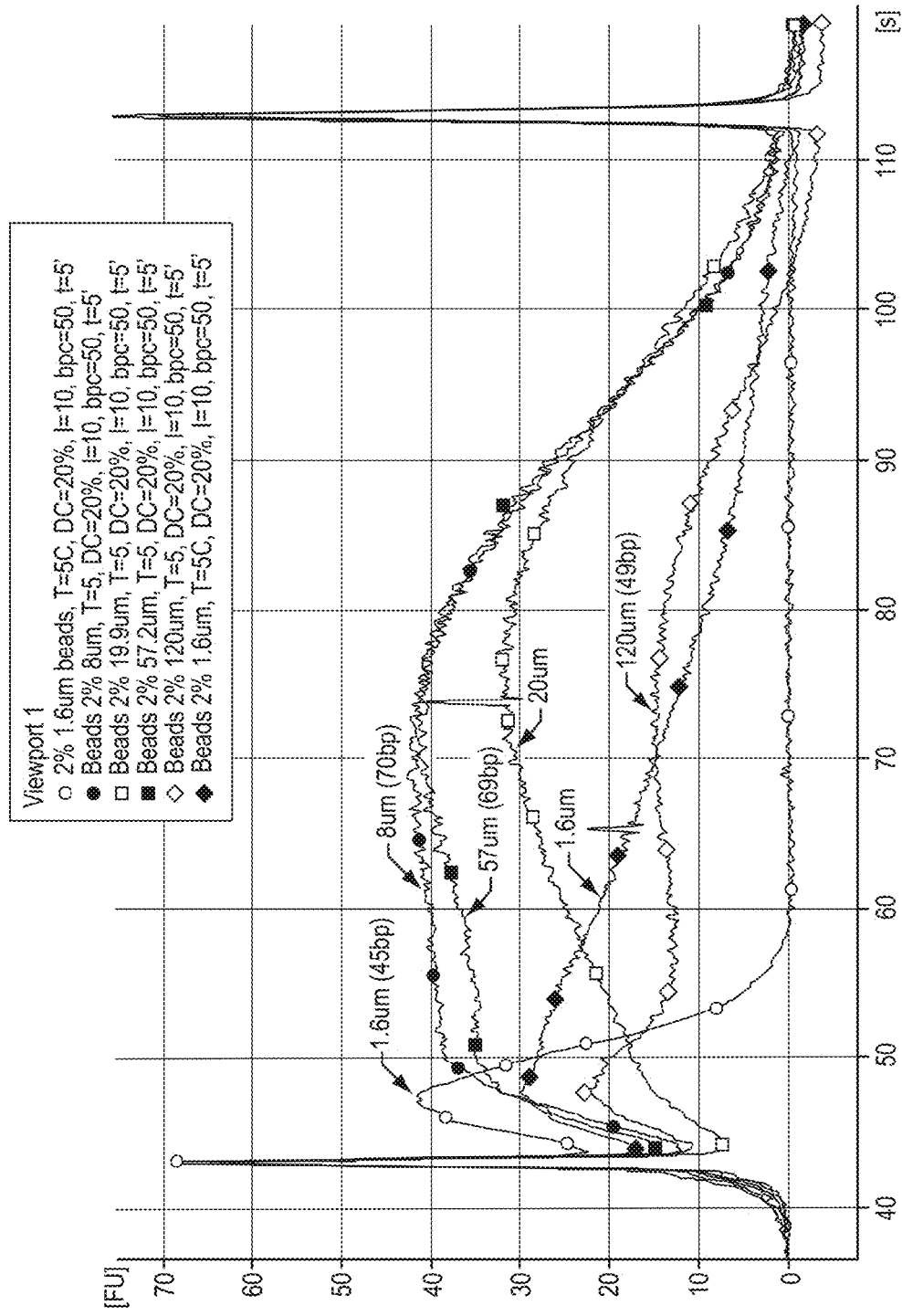
FIG. 8 shows a graph demonstrating the effects of particle size on fragmentation.
Figure 9:
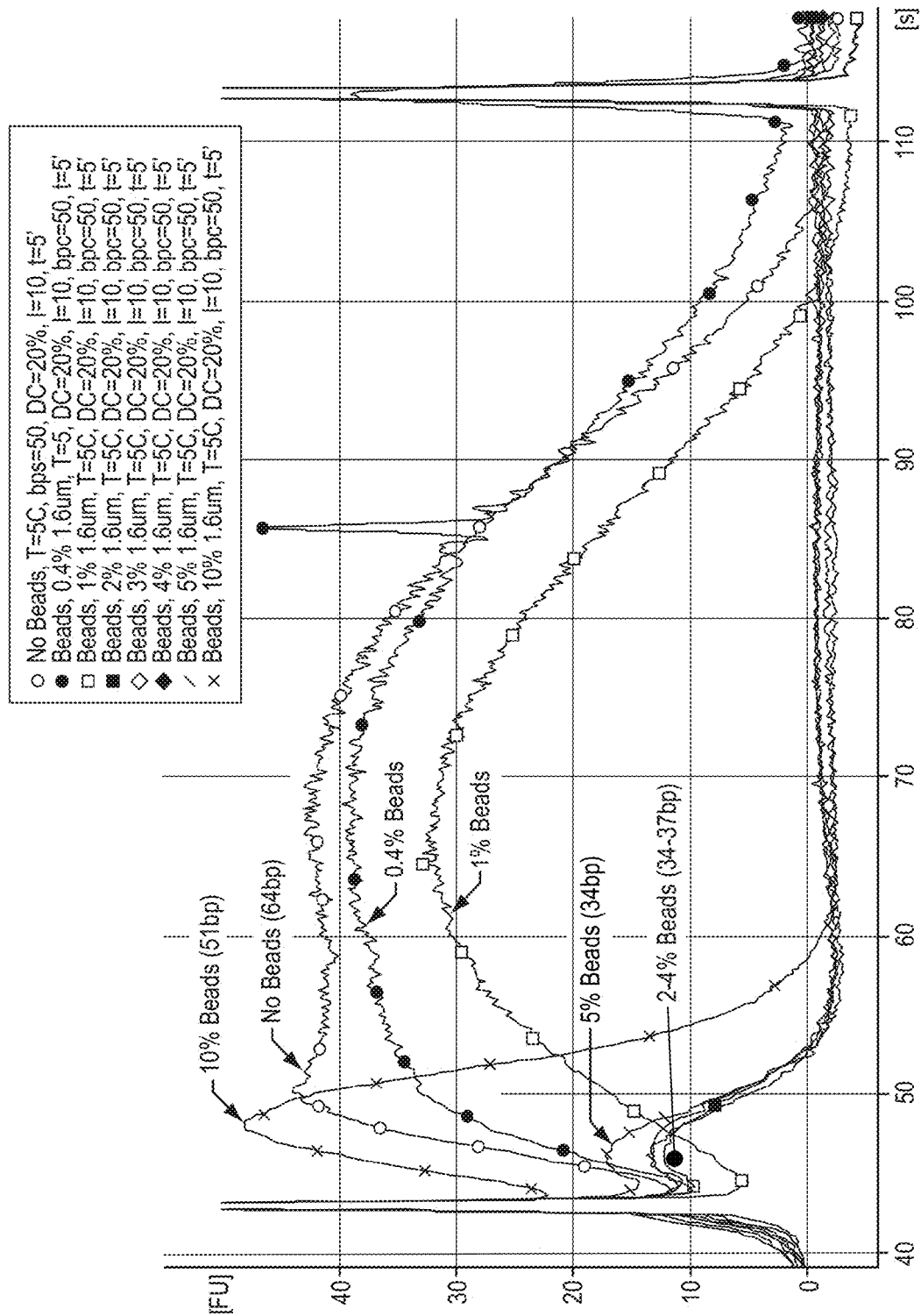
FIGS. 9, 10, and 17 show graphs demonstrating the effects of particle concentration on fragmentation.
Figure 10:
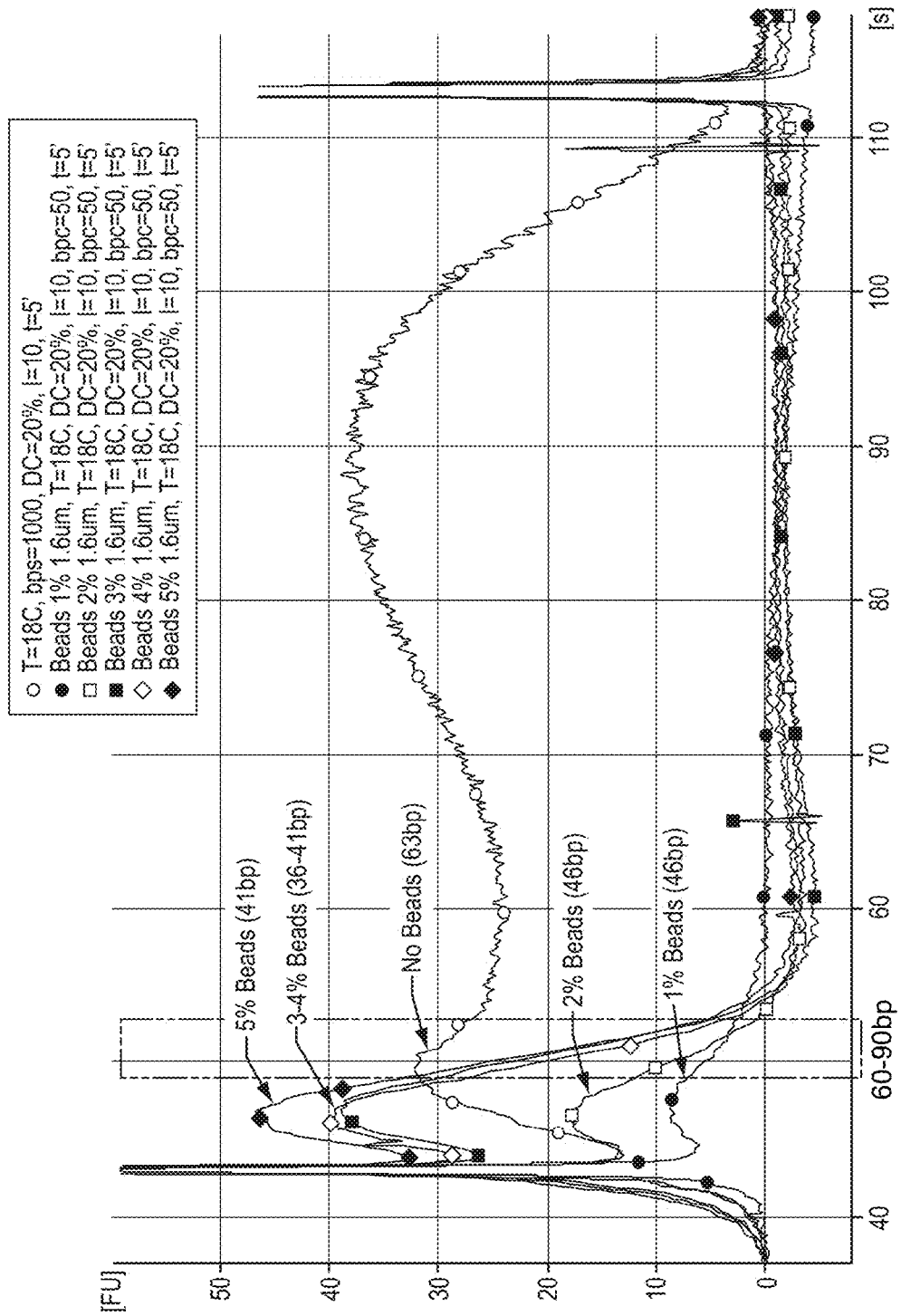
Figure 19:
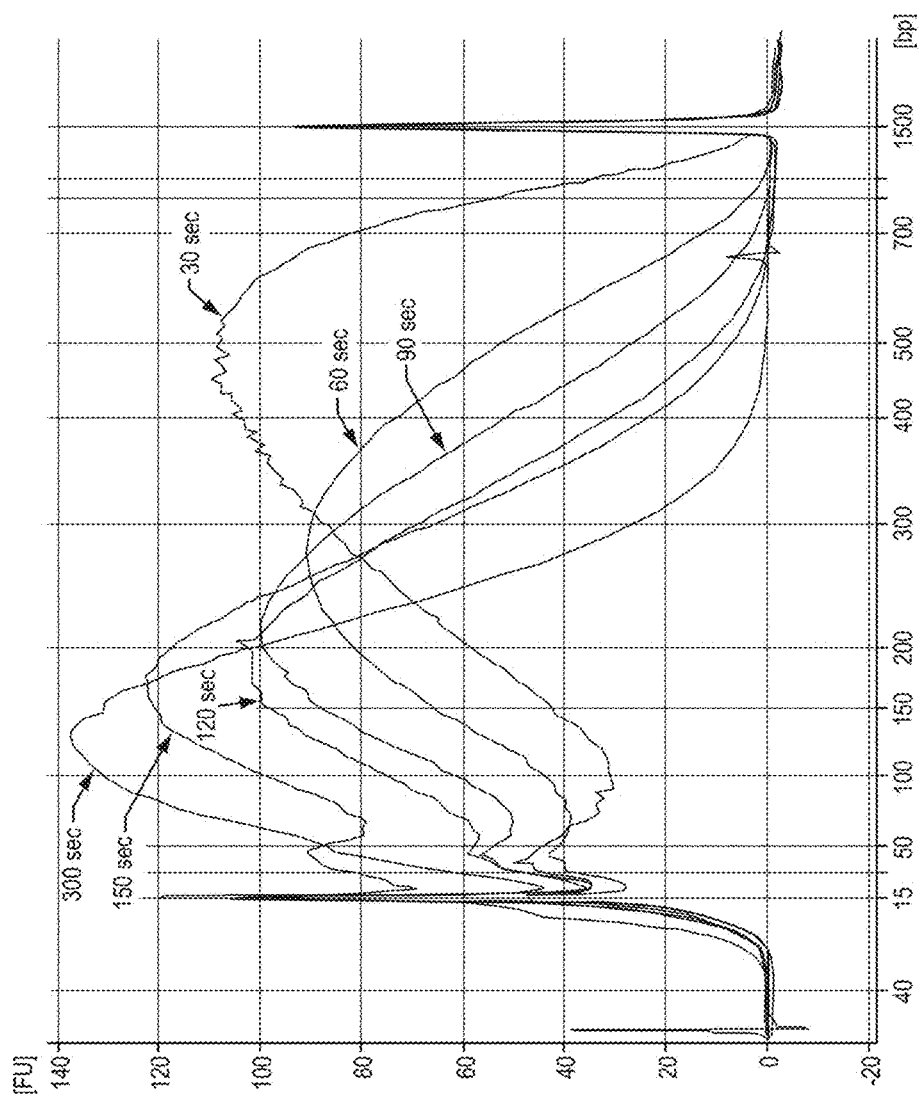

In various embodiments, the size of the particles can range from 0.1 micrometers to 100 micrometers and provide a concentration of 0.1% to 20% weight per volume during fragmentation. In various embodiments, FIG. 8 illustrates a graph showing the effect of particle size at a fixed concentration of 2%. This embodiment demonstrates that lower particle sizes, e.g. beads 1.6 micrometers to 8 micrometers of diameter, provided the desirable fragment sizes of 60 base pairs to 90 base pairs. In various embodiments, FIGS. 9 and 10 illustrate graphs showing the effect particle concentration at a fixed particle size of 1.6 micrometers at 5 degrees Celsius and 18 degrees Celsius, respectively. This embodiment demonstrated that particle concentration 2% to 5% provided the desirable fragment sizes. In various embodiments, FIG. 19 illustrates the dependence on time for fragmentation with 2.0 micrometer glass particles in glycerol-free solution.

Figure 11:
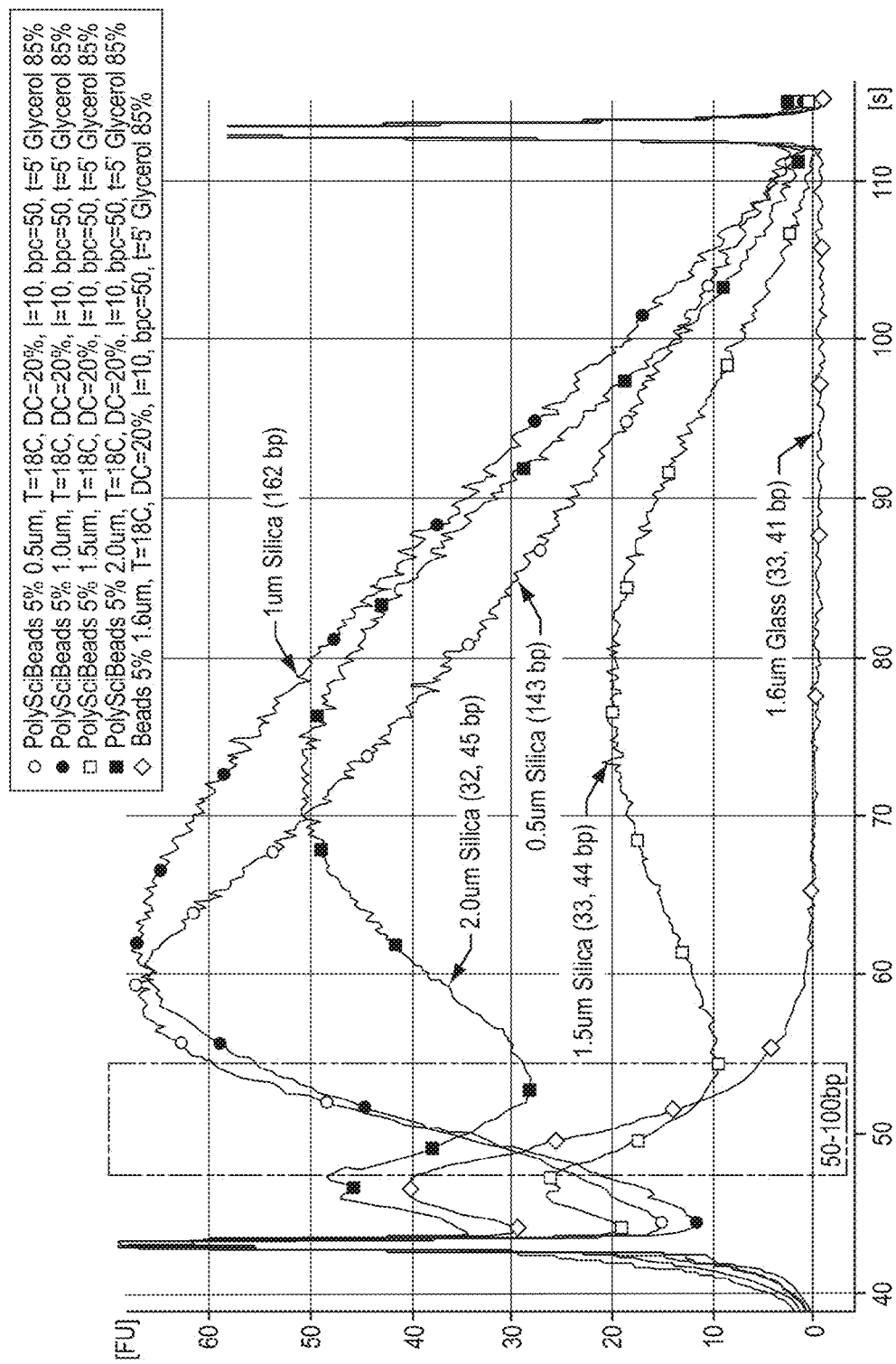
FIG. 11 shows a graph demonstrating the effects of particle material on fragmentation.
Figure 20:
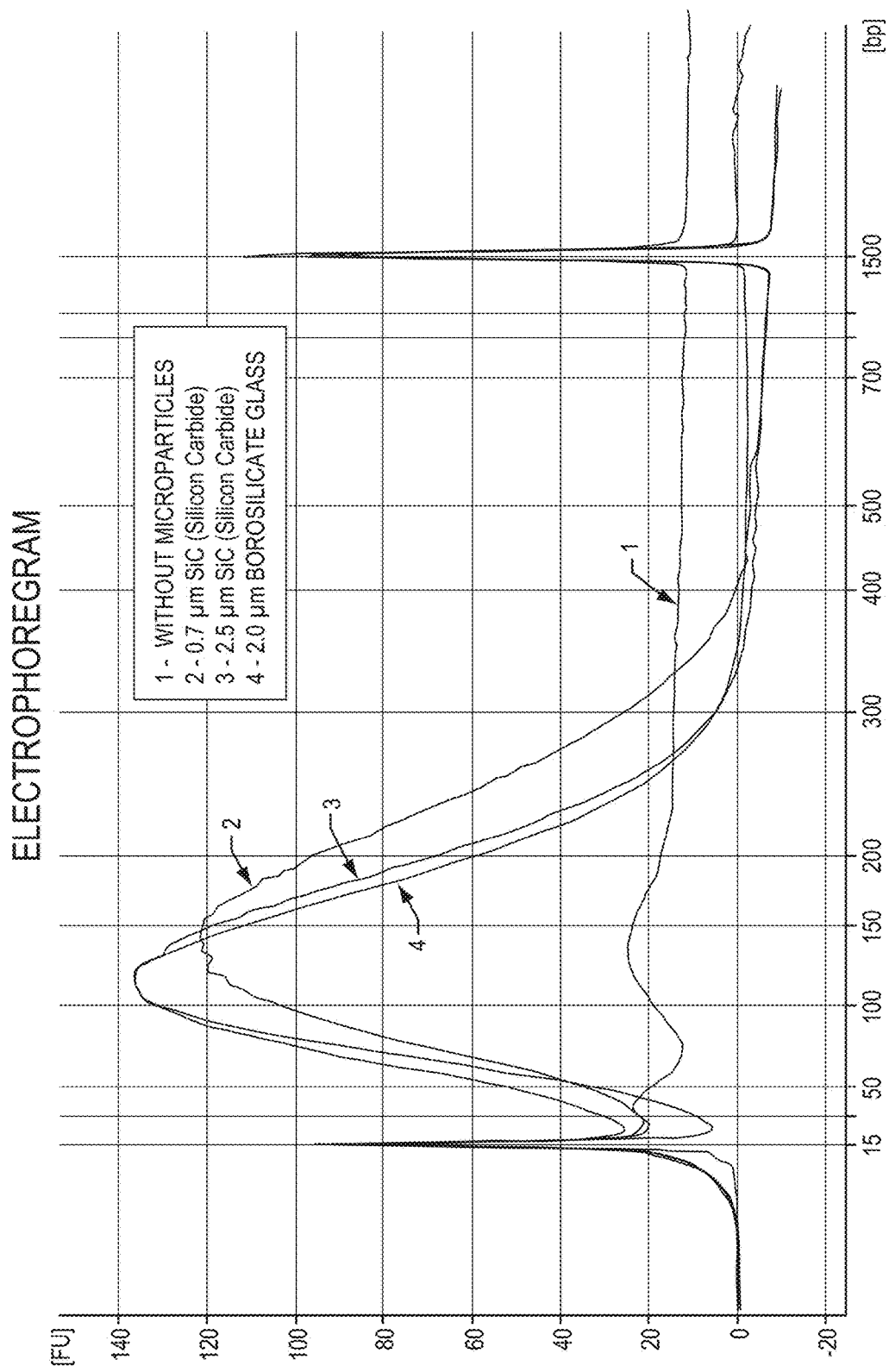
FIGS. 20 and 21 show a graph and a gel image to demonstrate different particle material effects on nucleic acid fragmentation.
Figure 21:
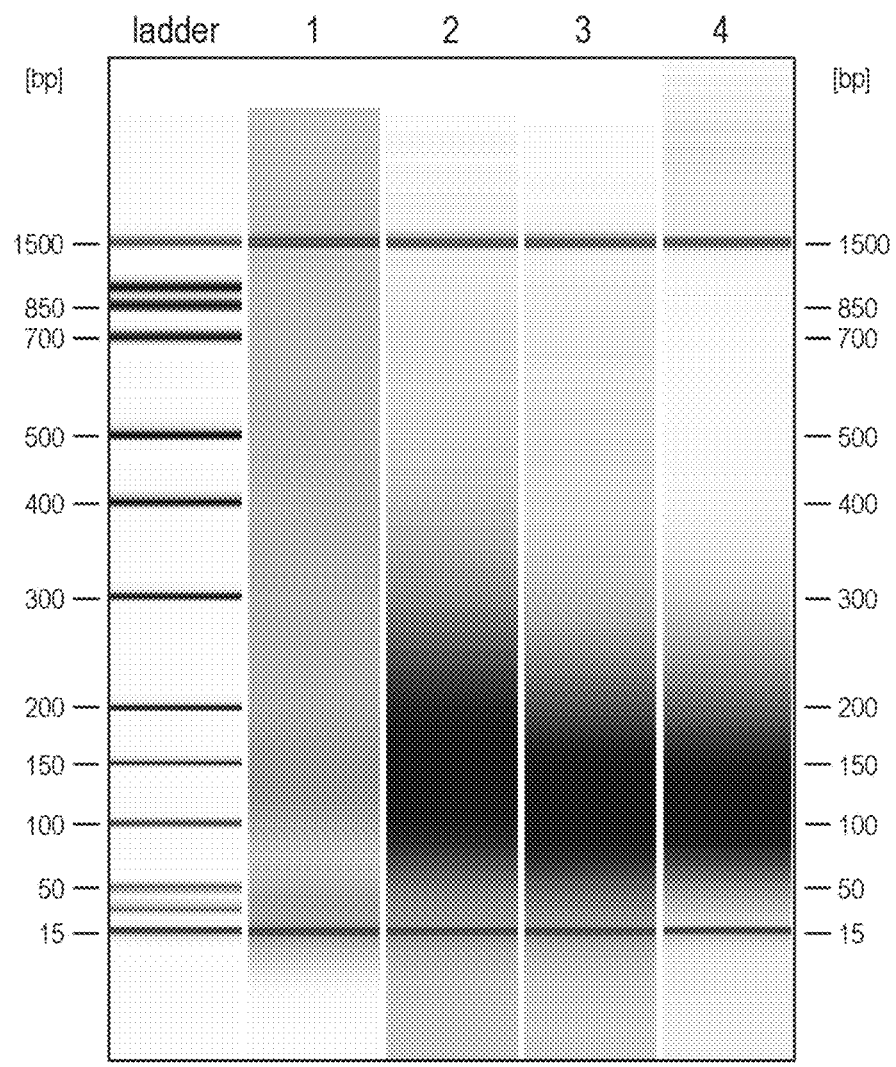

In various embodiments, the particles can be spherical or irregular shaped, non-porous or partial porosity, monodispersed or broadly dispersed over a size range. In various embodiments the composition of the particles can include glass (e.g. borosilicate glass), silicon carbide, silica, soda lime glass, diamond, metal (e.g. Ag, Au, Al, Co, Cu, Fe, Mo, Ni, Ti, W, Zn), metal oxides (e.g. $Al_2O_3$, $ZrO_2$, $HfO_2$, $TiO_2$, $CeO_2$, $SiO_2$ and mixed oxides), hollow ceramic, metal (e.g. Al or Ni) coated hollow ceramic or combinations thereof. In various embodiments, the particles can be non-magnetic or paramagnetic. In various embodiments, FIG. 11 illustrates a graph showing the effect of particle composition on fragmentation. This embodiment demonstrated that silica, even at particle sizes that had provided favorable fragmentation, did not fragment nucleic acids at the desired fragment sizes as did 1.6 micrometer glass particles. In various embodiments, FIGS. 20 and 21 illustrate silicon carbide and borosilicate glass as alternative compositions for the particles. Silicon carbide was obtained from Electro Abrasives Co. with a hardness of 9.6 (Moh) and a blocky, sharp shape and borosilicate glass from Duke Scientific Inc. with a hardness of 6.5 (Moh) and a spherical shape. FIG. 21 shows a gel electrophoresis showing the fragment size for the nucleic acid.

Figure 13:
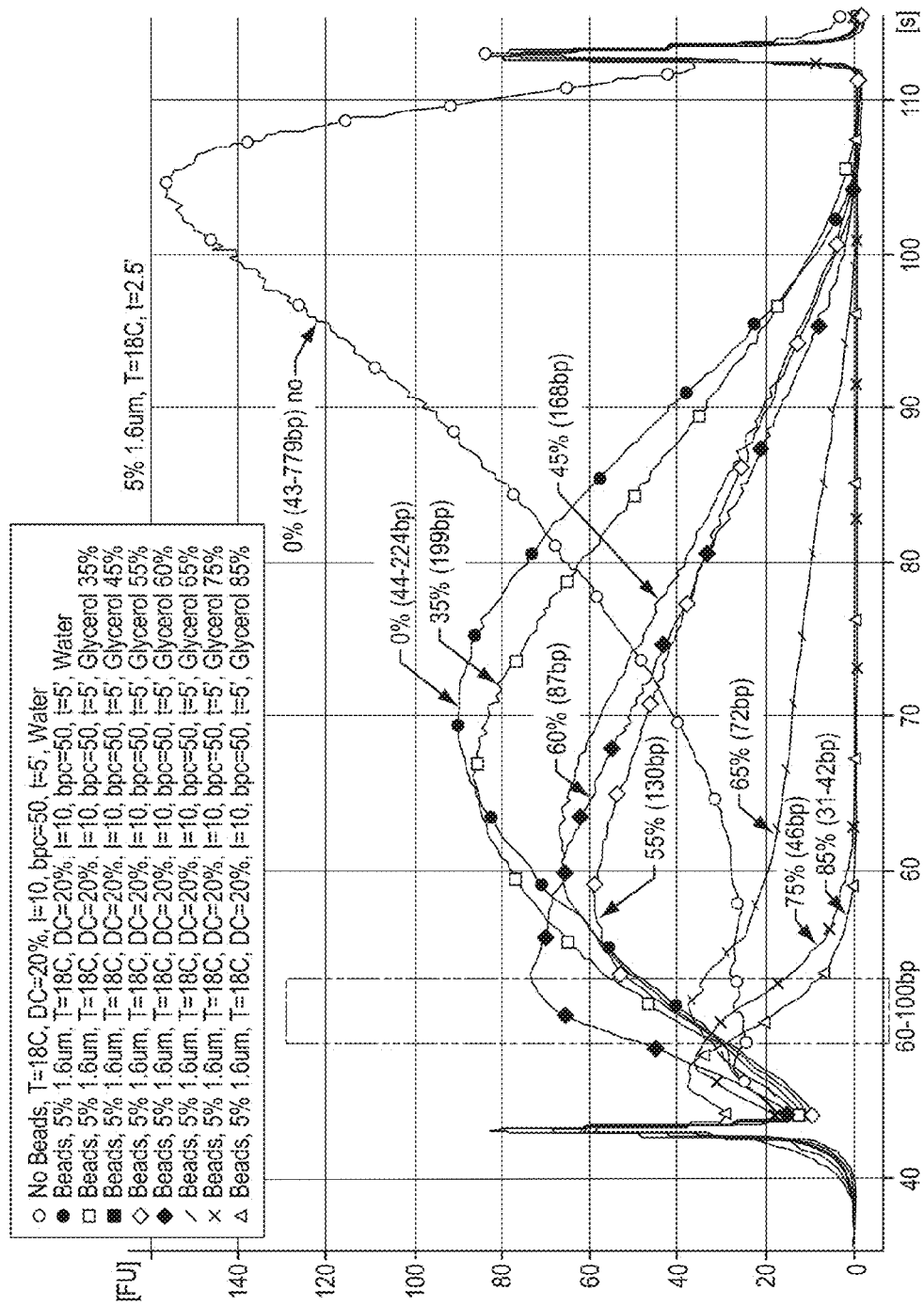
FIG. 13 shows a graph demonstrating the effects of viscosity of solvent on fragmentation.
Figure 14:
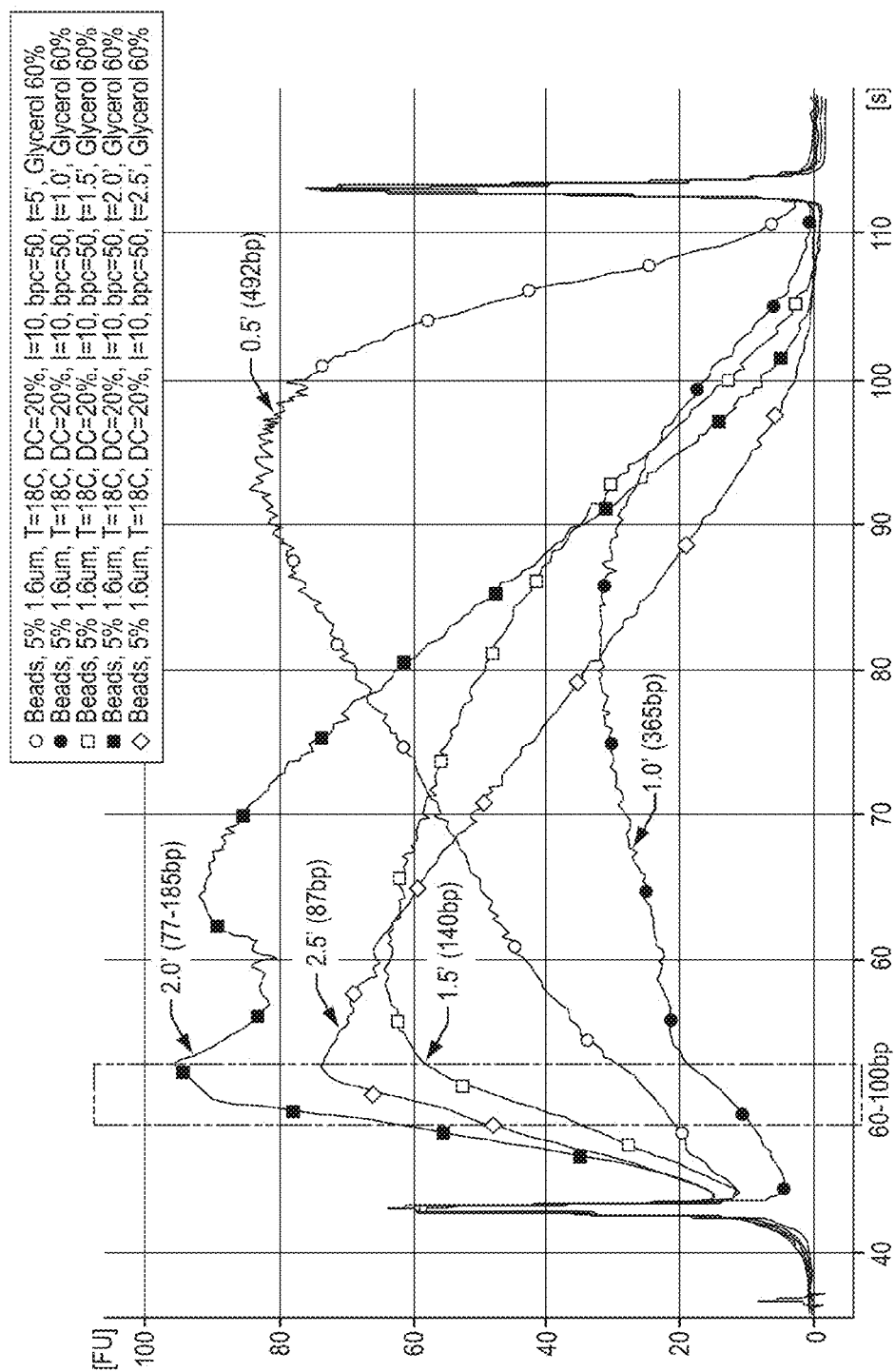

In various embodiments, it is desirable to reduce the concentration of glycerol to minimize losses of DNA during subsequent step of DNA-binding column purification, i.e. QIAGEN MinElute column, prior to end-repair of sonicated DNA provided to for example, sequencing analysis by, for example, SOLiD. Even more desirable is to fragment DNA in glycerol-free solution in order to couple the sheared DNA sample directly to the end-repair enzymatic reaction, thus, eliminating without the intermediate column step, which would further increase the yield of fragmented nucleic acid provided to for example, sequencing analysis by, for example, SOLiD. In various embodiments, FIG. 13 illustrates a graph showing the effect of glycerol concentration on fragmentation in the presence of glass beads. The sonication time was fixed for each sample to 2.5 minutes. This embodiment demonstrates that some concentration of glycerol particularly 60% to provide an effect (increased yield in the target range) at that time frame. In various embodiments, FIG. 14 illustrates a graph showing the effect of time at a fixed glycerol concentration of 60%. This embodiment demonstrates that increasing the sonication time provides fragments closer to the desirable fragment sizes. The following chart shows several embodiments for fragmentation by sonication with different concentrations of glycerol as compared to nebulization.

| Treatment | Method | Time | Glycerol | Beads |
|---|---|---|---|---|
| C1 | Covaris | 2' | 60% | 5%* 1.6 um (Duke#145) |
| C9 | Covaris | 30' | 0% | 5%* 1.6 um (Duke#145) |
| N1 | Nebulizer (75 psi) | 15' | 75% | None |
| Solid | Covaris | 40' | 85% | None |

Figure 15:
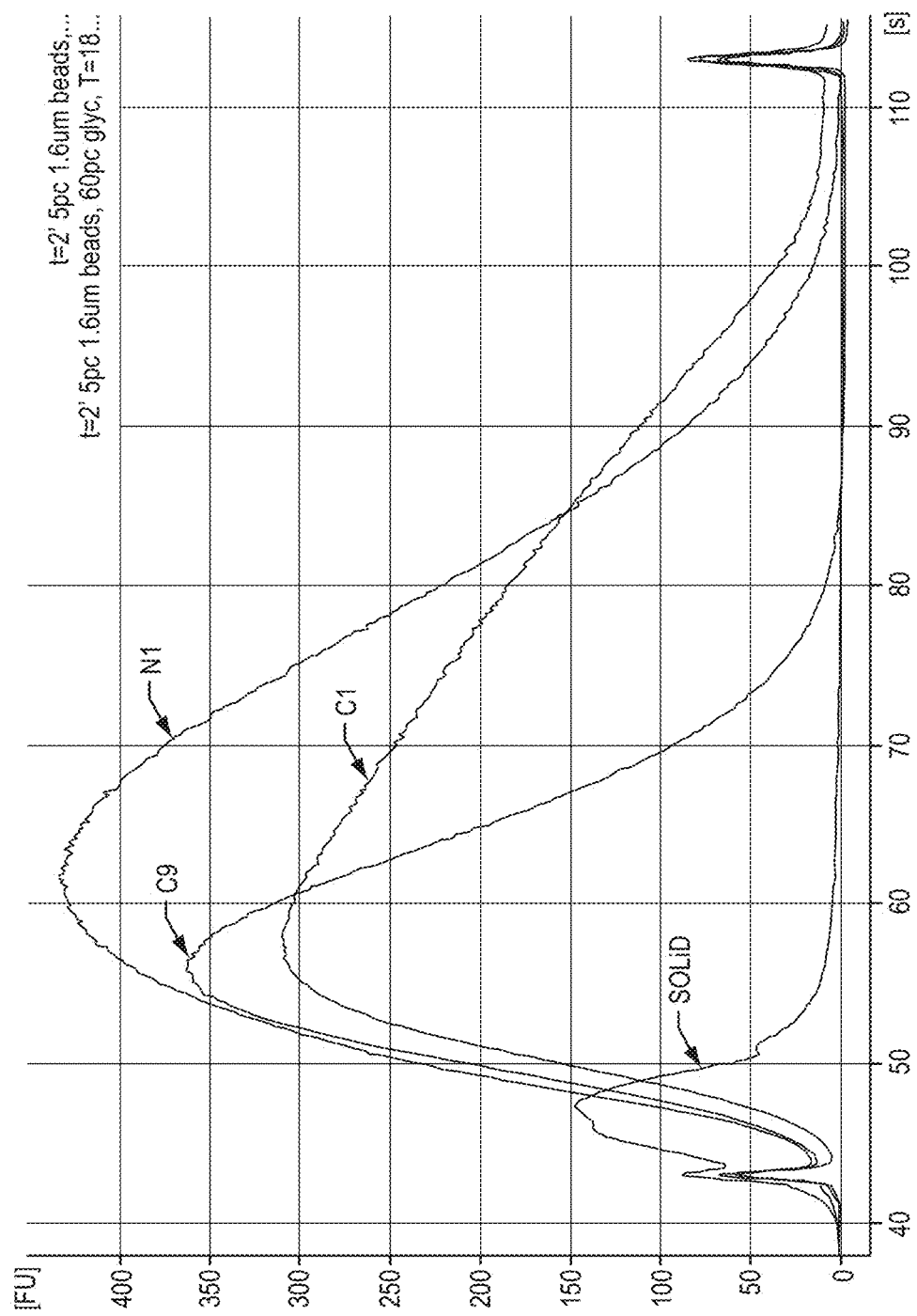
FIGS. 15 through 16 shows graphs demonstrating fragment size distribution and the yield of recovered fragmented DNA depending on fragmentation method used in some embodiments of present invention.
Figure 16:
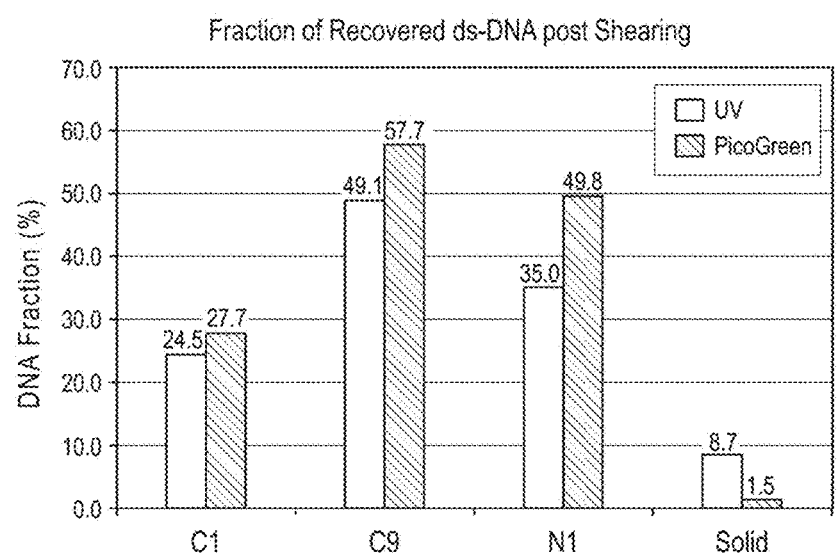

In various embodiments, FIG. 15 illustrates a graph with nucleic acid fragment size distribution generated under conditions shown in the above chart. This embodiment demonstrates that sonication without glycerol or less glycerol than 85% provides better yields of nucleic acid fragments in the desired size range for subsequent analysis. FIG. 167 illustrates a comparison of yield of total and double stranded DNA ethanol precipitated after fragmentation by different methods. UV absorbance measures total yield of nucleic acid (single stranded DNA, double stranded DNA, and free nucleotides combined), while, PicoGreen is highly selective for double stranded DNA. Only double-stranded DNA generated during fragmentation step will serve as a substrate for further steps of library construction. As evident from the FIG. 16 the highest yield of total and double stranded DNA is achieved with method C9. In contrast, the standard SOLiD method results in significant losses due to overshearing and thermal denaturation of DNA—only 8.7% of input DNA is recovered with 17% of that in double stranded form. The following chart illustrates a comparison for quantity of double stranded DNA in a target size range captured by the different embodiments.

| Treatment | Time | Glycerol | Beads | 60-90bp ds-DNA (ng) |
|---|---|---|---|---|
| C1 | 2' | 60% | 5% 1.6 um | 196 |
| C9 | 30' | 0% | 5% 1.6 um | 785 |
| N1 | 15' | 75% | None | 254 |
| V(Solid) | 40' | 85% | None | 15.5 |

Figure 17:
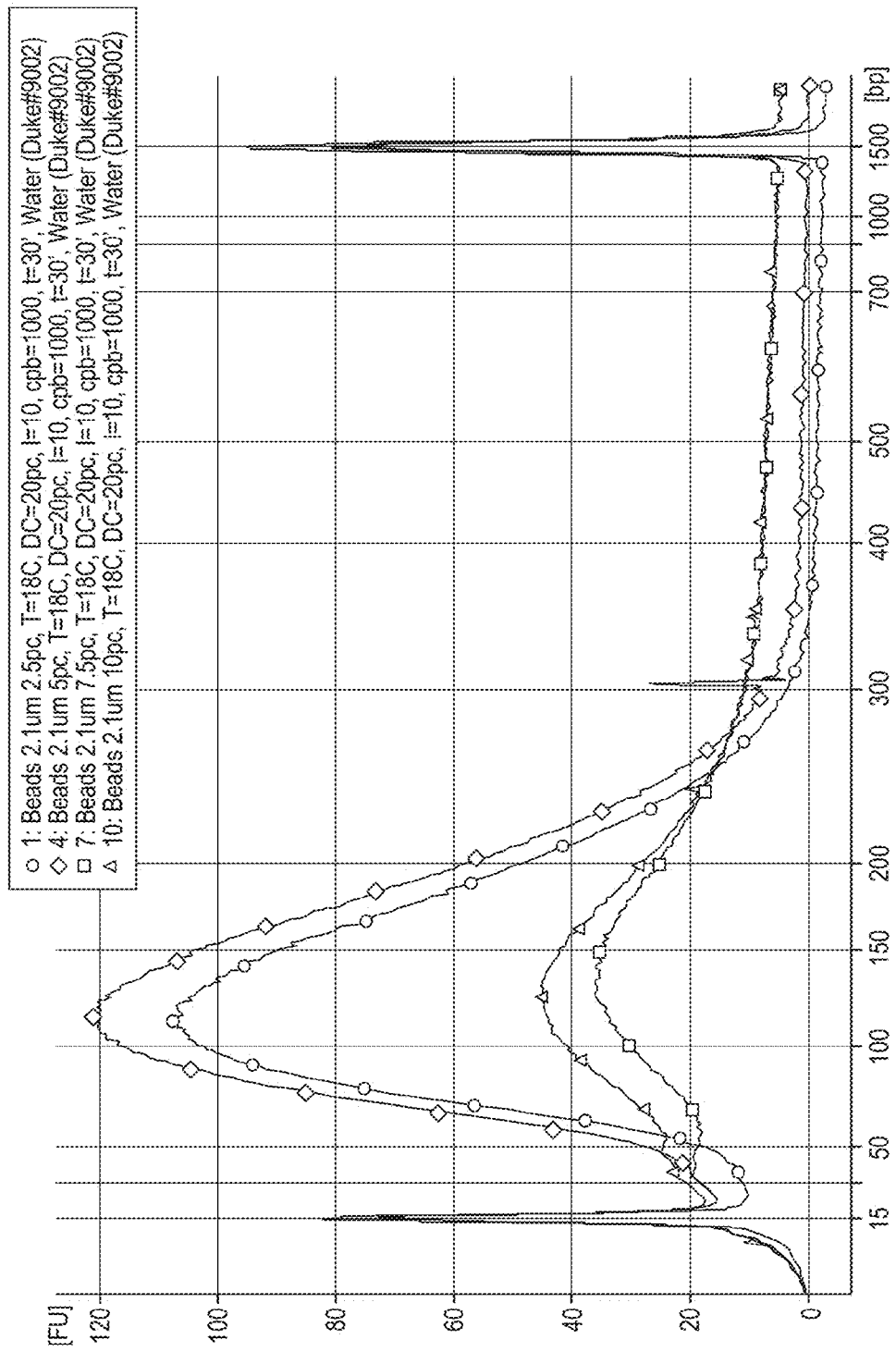
Figure 18:
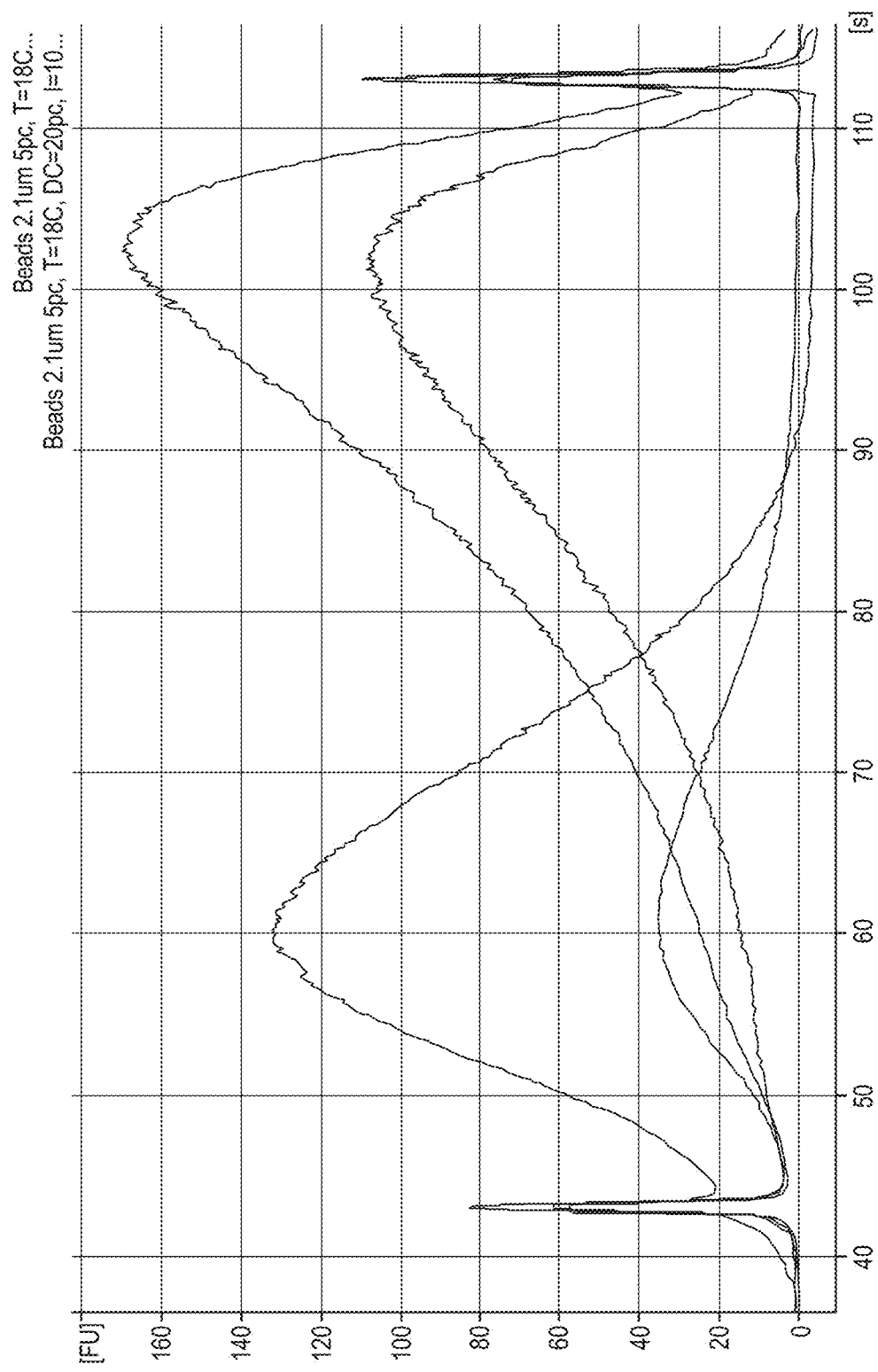
FIG. 18 shows a graph demonstrating the effects of different amounts of purified nucleic acid on fragmentation.
Figure 22:
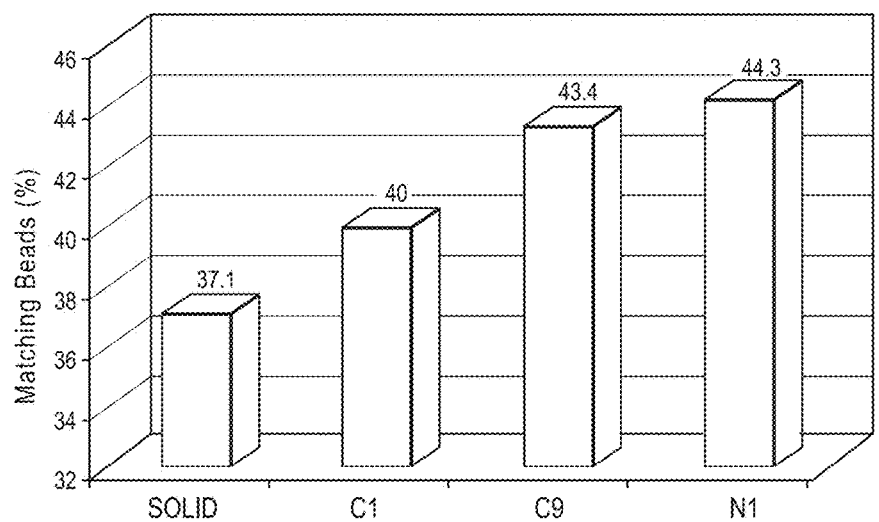
FIG. 22 shows the quality of SOLiD sequencing results of fragment libraries constructed using different DNA shearing methods.

The sequencing data captured shown in the FIG. 22 shows the improved yield of Matching Beads (as percentage of Readable Beads) in C9 method compared to SOLiD method, demonstrating that the sequencing data of better quality is obtained when using the combination of glycerol-free solution with microbeads. In various embodiments, the graph in FIG. 17 shows an effect of bead concentration on fragmentation of the nucleic acid in an aqueous solution with out non-aqueous solvent such as glycerol.

Figure 23:
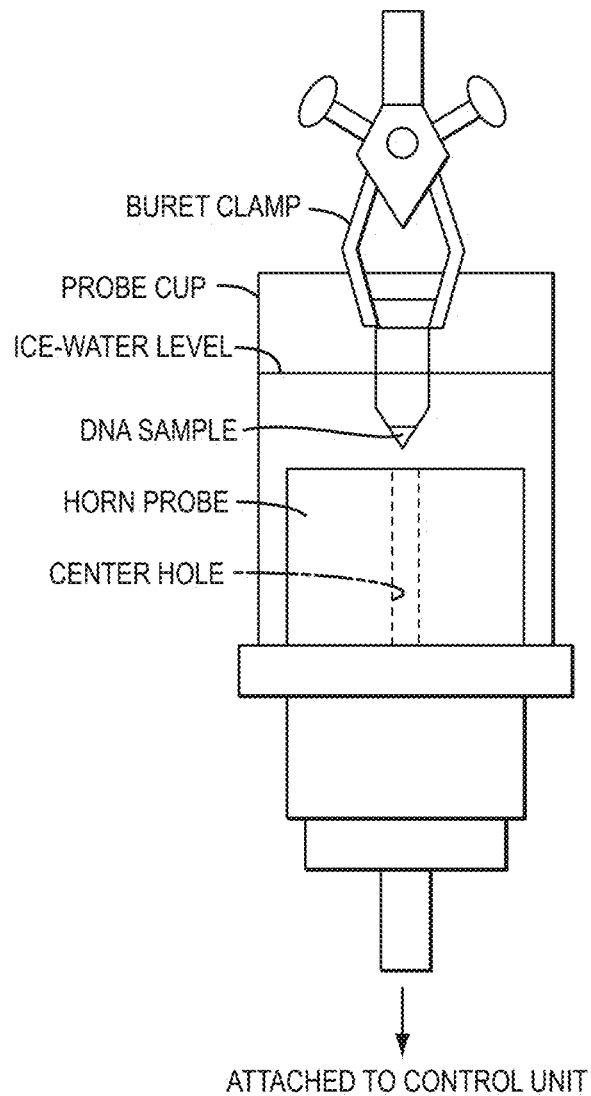
FIG. 23 shows a schematic of the cup-and-horn sonicator used to shear DNA and to produce the data in the following figures

FIG. 23 shows a schematic representation of ing a cup and horn sonicator. A sonicator of the cup-and-horn type is traditionally used to shear DNA down to sizes of ~500 bp. It is well known that the amount of ds-DNA and its integrity dramatically decreases decrease if this method is used to obtain shorter fragments. (CSH protocols, 2006).

Figure 24:
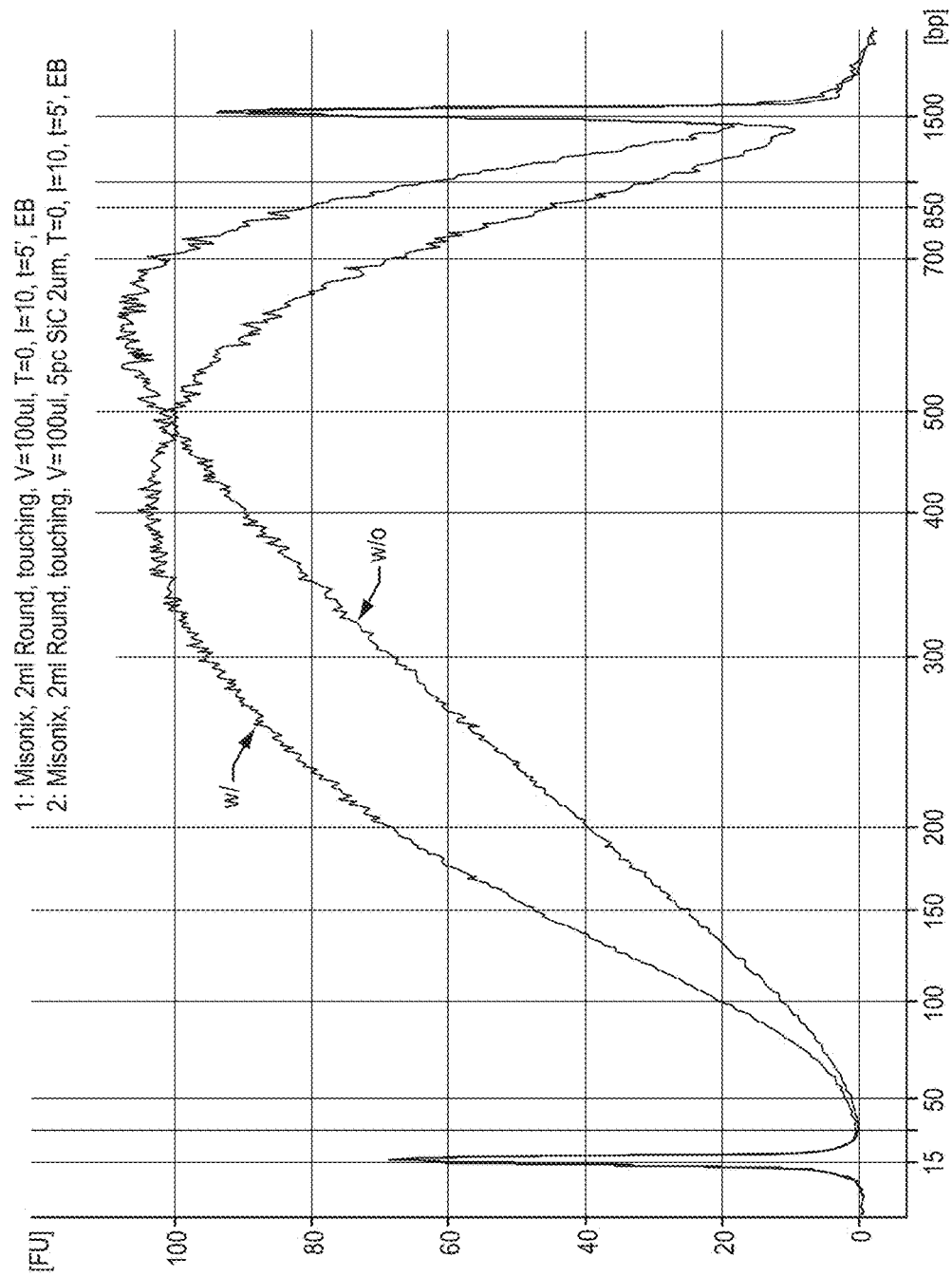
FIG. 24 shows a graph of DNA fragmentation comparing existing methods ("w/o") and non-limiting exemplary methods ("w") of the present invention. The fragmentation was performed with a 5' run in a 2 ml round bottom Eppendorf tube in a Misonix cup-and-horn sonicator.

FIG. 24 shows the distribution of DNA fragment sizes obtained after shearing DNA for 5 minutes' at continuous maximum intensity in a Misonix 3000 cup and horn sonicator. The curve marked "w" was obtained with an embodiment consisting of 5% Silicon Carbide beads of 2 um average size obtained from Electroabrasives and suspended in 200 ul of aqueous buffer placed in a 2 ml round bottom Eppendorf tube, while the one marked "w/o" was obtained using the traditional method, subjecting the sample to the same conditions but without beads. This figure demonstrates that fragments 30% shorter at the distribution peak can be achieved with this embodiment (400 vs 600 bp).

Figure 25:
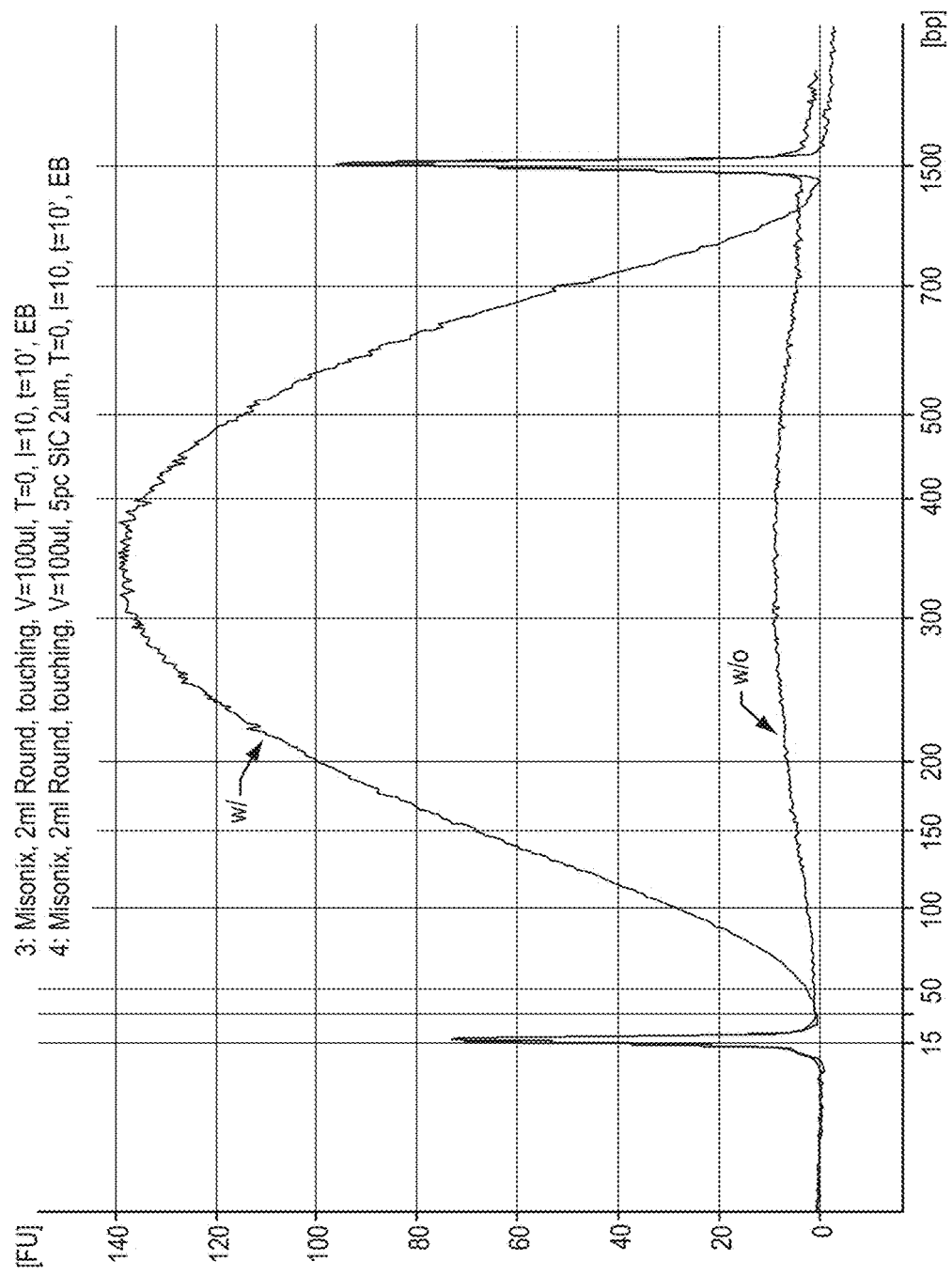
FIG. 25 shows a graph of DNA fragmentation comparing existing methods ("w/o") and non-limiting exemplary methods ("w") of the present invention. The fragmentation was performed with a 10' run in a 2 ml round bottom Eppendorf tube in a Misonix cup-and-horn sonicator.

FIG. 25 shows the distribution of DNA fragment sizes obtained after shearing DNA for 10 minutes at continuous maximum intensity in a Misonix 3000 cup and horn sonicator. The curve marked "w" was obtained with an embodiment consisting of 5% Silicon Carbide beads of 2 um average size obtained from Electroabrasives and suspended in 200 ul of aqueous buffer placed in a 2 ml round bottom Eppendorf tube, while the one marked "w/o" was obtained using the traditional method, subjecting the sample to the same conditions but without beads. This figure demonstrates that without the embodiment claimed in this invention the DNA greatly denatures and only a small fraction of the input material survives sonication. On the other hand, when the non-limiting described embodiment is used, the amount of sheared DNA in double stranded form is preserved, thus providing a large yield. In general, to prevent DNA from denaturing, the ultrasonic energy is applied intermittently in pulses to allow the liquid to cool down in between pulses, thus mitigating the thermally induced DNA denaturing process. This translates into a longer processing time: for example, if a duty cycle of 0.5 is used, the total processing time will be twice as long. A clear benefit of this non-limiting embodiment is that sonication can be applied at continuous maximum power to the sample without it undergoing measurable degradation.

Figure 26:
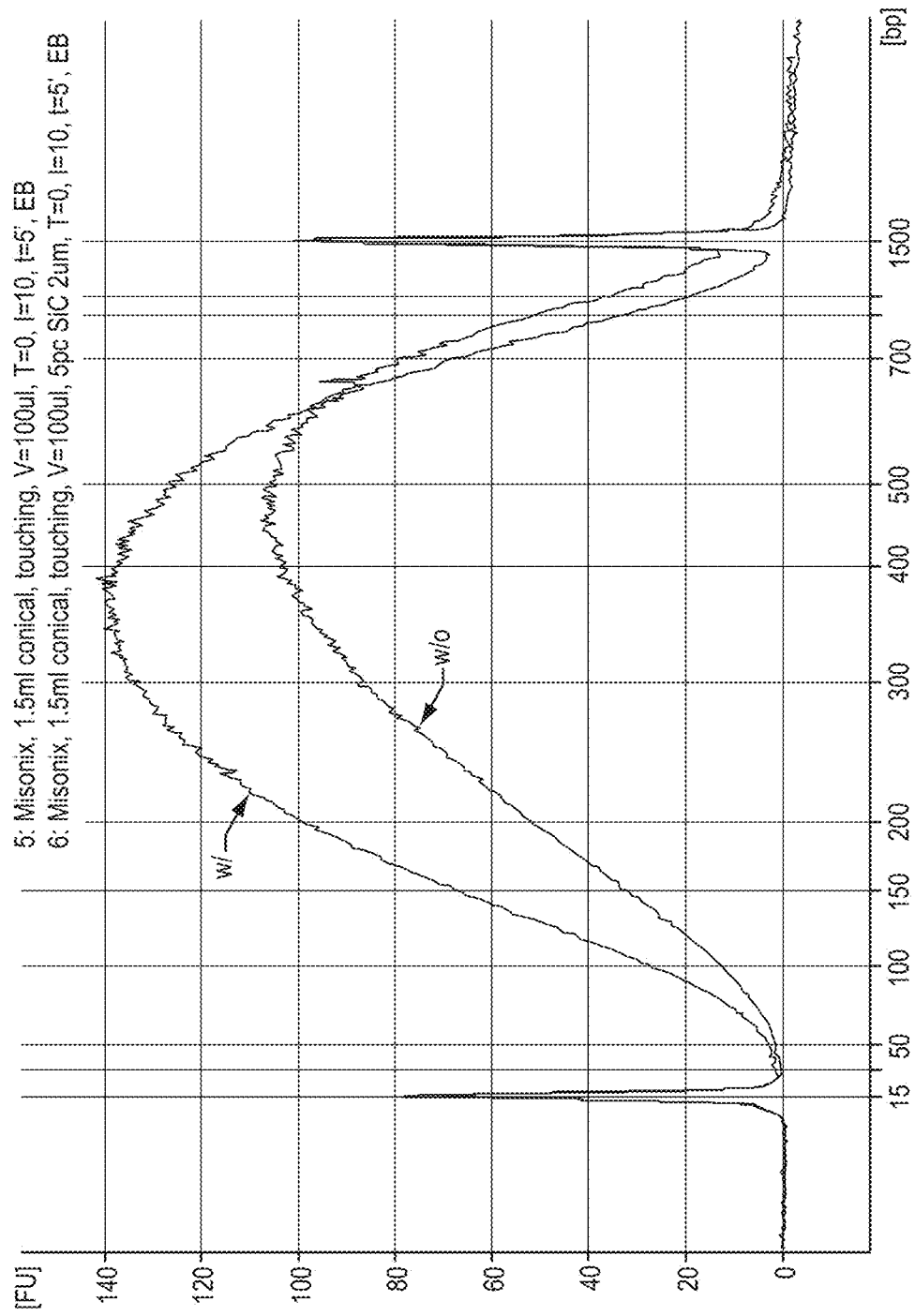
FIG. 26 shows a graph of DNA fragmentation comparing existing methods ("w/o") and non-limiting exemplary methods ("w") of the present invention. The fragmentation was performed with a 5' run in a 1.5 ml conical bottom Eppendorf tube in a Misonix cup-and-horn sonicator.

FIG. 26 shows the distribution of DNA fragment sizes obtained after shearing DNA for 5 minutes at continuous maximum intensity in a Misonix 3000 cup and horn sonicator. The curve marked "w" was obtained with an embodiment consisting of 5% Silicon Carbide beads of 2 um average size obtained from Electroabrasives and suspended in 200 ul of aqueous buffer placed in a 1.5 ml conical bottom Eppendorf tube, while the one marked "w/o" was obtained using the traditional method, subjecting the sample to the same conditions but without beads. This figure demonstrates that fragments 30% shorter at the distribution peak can be achieved with this embodiment (400 vs 600 bp).

Figure 27:
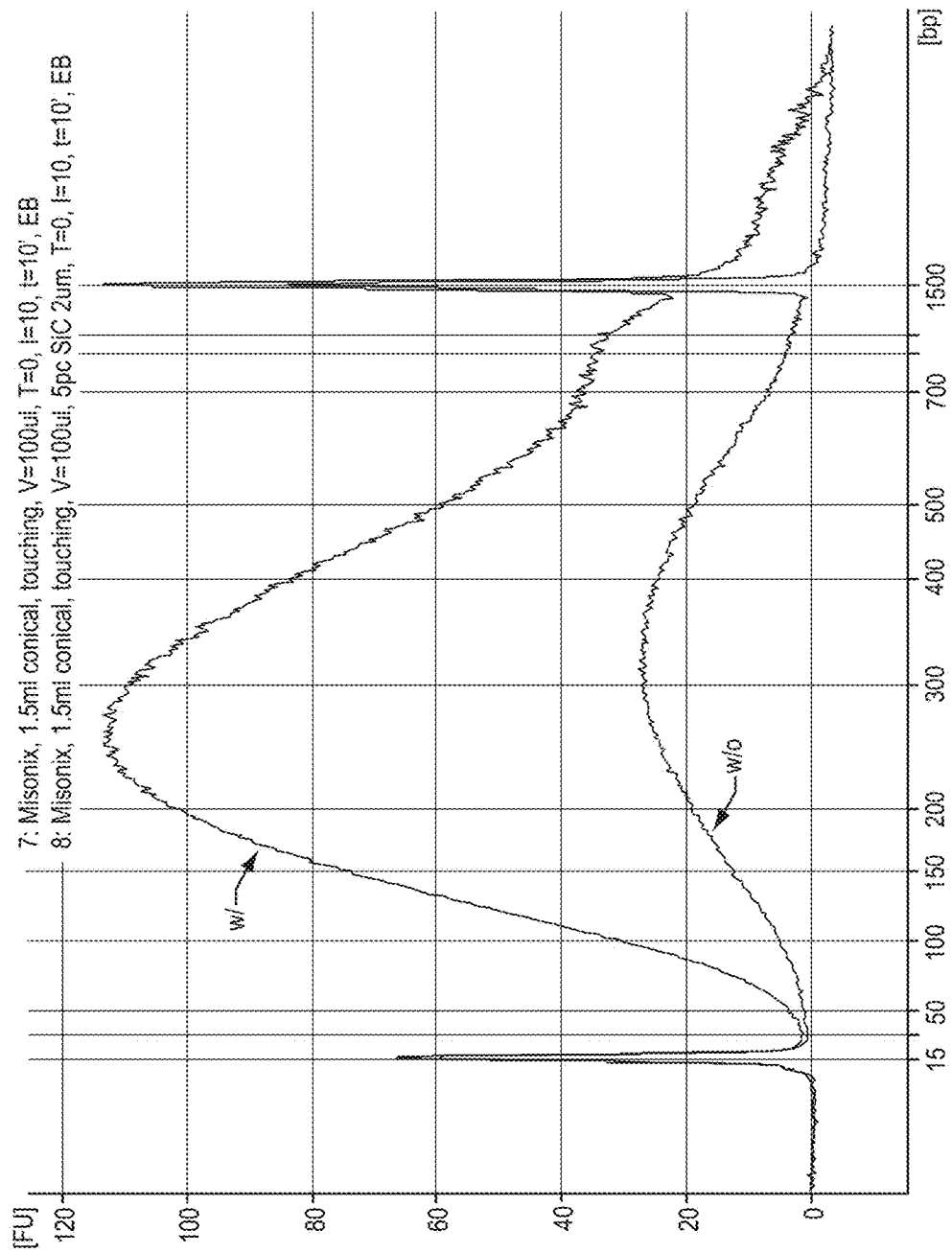
FIG. 27 shows a graph of DNA fragmentation comparing existing methods ("w/o") and non-limiting exemplary methods ("w") of the present invention. The fragmentation was performed with a 10' run in a 1.5 ml conical bottom Eppendorf tube in a Misonix cup-and-horn sonicator.

FIG. 27 shows the distribution of DNA fragment sizes obtained after shearing DNA for 10 minutes at continuous maximum intensity in a Misonix 3000 cup and horn sonicator. The curve marked "w" was obtained with an embodiment consisting of 5% Silicon Carbide beads of 2 um average size obtained from Electroabrasives and suspended in 200 ul of aqueous buffer placed in a 1.5 ml conical bottom Eppendorf tube, while the one marked "w/o" was obtained using the traditional method, subjecting the sample to the same conditions but without beads. This figure demonstrates that without the embodiment claimed in this invention the DNA greatly denatures and only a small fraction of the input material survives sonication. On the other hand, when the non-limiting described embodiment is used, the amount of sheared DNA in double stranded form is preserved, thus providing a large yield.

What is claimed:

1. A composition, comprising: an aqueous buffer solution which is substantially free of glycerol, monodisperse glass particles being 1.6-8 microns in diameter; and purified nucleic acids.

2. The composition of claim 1, wherein the monodisperse particles are present at 0.1% to 20% weight per volume when mixed with the aqueous buffer solution.

3. The composition of claim 1, wherein the aqueous buffer solution comprises Tris and EDTA and has a pH of 7.5 to 8.0.

4. The composition of claim 1, wherein the purified nucleic acids comprise genomic DNA that is free of cellular lysate.

5. The composition of claim 1, wherein the purified nucleic acids comprise chromatin that is free of cellular lysate.

6. The composition of claim 1, comprising 2-5% weight per volume of the monodisperse glass particles.

7. The composition of claim 1, wherein the monodisperse glass particles comprise a blocky sharp shape and a hardness of 9.6 (Moh).

8. The composition of claim 1, wherein the monodisperse glass particles comprise a spherical shape and a hardness of 6.5 (Moh).

9. The composition of claim 1, wherein the monodisperse glass particles are non-magnetic.

10. The composition of claim 1, further comprising a sonicator.

11. The composition of claim 10, wherein the sonicator comprises a focusing acoustic sonicator.

* * * * *